United States Patent [19]

Takizawa et al.

[11] Patent Number: 4,465,835
[45] Date of Patent: Aug. 14, 1984

[54] DIBENZ [B,E] OXEPIN DERIVATIVES

[75] Inventors: Hiroshi Takizawa; Osamu Morita; Yoshimasa Oiji; Tamotsu Hashimoto, all of Shizuoka, Japan

[73] Assignee: Kyowa Hakko Kogyo Co., Ltd., Tokyo, Japan

[21] Appl. No.: 486,425

[22] Filed: Apr. 19, 1983

Related U.S. Application Data

[62] Division of Ser. No. 256,037, Apr. 21, 1981, Pat. No. 4,396,550.

[30] Foreign Application Priority Data

Apr. 22, 1980 [JP] Japan .................................. 55-52261
Apr. 22, 1980 [JP] Japan .................................. 55-52262

[51] Int. Cl.³ .......................................... C07D 405/04
[52] U.S. Cl. .................................................. 546/133
[58] Field of Search ........................................ 546/133

[56] References Cited

U.S. PATENT DOCUMENTS 3,458,516  7/1969  Howell et al. ..................... 260/333
3,509,176  4/1970  Winter et al. ..................... 260/333
3,872,102  3/1975  Malen et al. ...................... 260/333

Primary Examiner—Richard Raymond
Attorney, Agent, or Firm—Fitzpatrick, Cella, Harper & Scinto

[57] ABSTRACT

Novel dibenz [b,e] oxepin derivatives represented by the general formula:

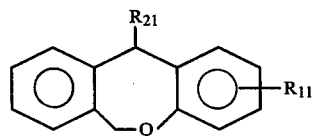

(Ia)

wherein $R_{11}$ represents an alkyl group containing 1 to 5 carbon atoms, an alkoxy group containing 1 to 5 carbon atoms, a halogen atom, a cyclohexyl group or a phenyl group; and $R_{21}$ represents

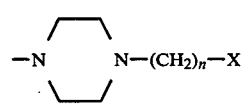
(1)

wherein X represents a hydrogen atom, a hydroxy group, an amino group or a substituted aralkyl group containing 7 to 20 carbon atoms, and n represents 0 or an integer of 1 to 3

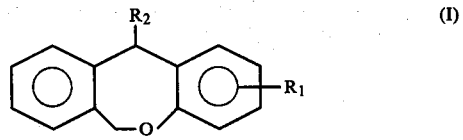

wherein Y represents an alkylamino group containing 1 to 5 carbon atoms, an aralkyl group containing 7 to 20 carbon atoms, a substituted aralkyl group, an aralkyloxy group containing 7 to 20 carbon atoms, an aralkylamino group containing 7 to 20 carbon atoms, a heterocyclic ring or a substituted heterocyclic ring, and n has the same meaning as defined before; provided that when $R_{11}$ represents an alkyl group, an alkoxy group or a halogen atom, X does not represent a hydrogen atom; and the pharmaceutically acceptable acid addition salts thereof.

Also disclosed are pharmaceutical compositions comprising a pharmaceutical carrier and, as an active ingredient, an effective amount of dibenz [b,e] oxepin derivative represented by the following general formula:

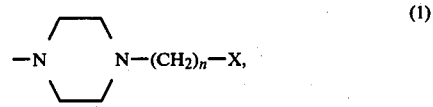

(I)

wherein $R_1$ represents an alkyl group containing 1 to 5 carbon atoms, an alkoxy group containing 1 to 5 carbon atoms, a halogen atom, a cyclohexyl group or a phenyl group; and $R_2$ represents

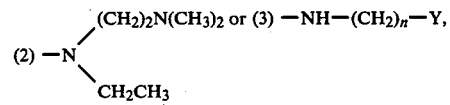
(1)

wherein X represents a hydrogen atom, a hydroxy group, an amino group or a substituted aralkyl group containing 7 to 20 carbon atoms, and n has the same meaning as defined before $$(2) -N\begin{matrix}(CH_2)_2N(CH_3)_2 \text{ or } (3) -NH-(CH_2)_n-Y,\\ CH_2CH_3\end{matrix}$$

wherein Y and n have the same meaning as defined above; and the pharmaceutically acceptable acid addition salts thereof. Compound I, represented by the general formula (I), has antichlolinergic, antihistaminergic, antiasthmatic and antiplatelet aggregation activities, and is therefore useful as a sposmolysant, an antihistaminic, an antiasthmatic agent and as a medicament for cardiovascular or cerebrovascular diseases, respectively.

9 Claims, No Drawings

DIBENZ [B,E] OXEPIN DERIVATIVES

This is a division of application Ser. No. 256,037, filed Apr. 21, 1981, now U.S. Pat. No. 4,396,550.

DETAILED DESCRIPTION OF THE INVENTION

This invention relates to novel dibenz [b,e] oxepin derivatives, the pharmaceutically acceptable acid addition salts thereof and a pharmaceutical composition containing, as the active ingredient, a dibenz [b,e] oxepin derivative.

More particularly, the present invention pertains to a novel dibenz [b,e] oxepin derivative represented by the following general formula (Ia):

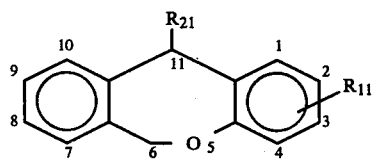

wherein $R_{11}$ represents an alkyl group containing 1 to 5 carbon atoms, an alkoxy group containing 1 to 5 carbon atoms, a halogen atom, a cyclohexyl group or a phenyl group; and $R_{21}$ represents

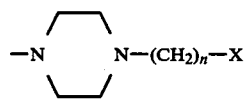

wherein X represents a hydrogen atom, a hydroxy group, an amino group or a substituted aralkyl group containing 7 to 20 carbon atoms, and n represents 0 or an integer of 1 to 3

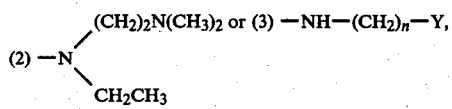

wherein Y represents an alkylamino group containing 1 to 5 carbon atoms, an aralkyl group containing 7 to 20 carbon atoms, a substituted aralkyl group, an aralkyloxy group containing 7 to 20 carbon atoms, an aralkylamino group containing 7 to 20 carbon atoms, a heterocyclic ring or a substituted heterocyclic ring, and n has the same meaning as defined before; provided that when $R_{11}$ represents an alkyl group, an alkoxy group or a halogen atom, X does not represent a hydrogen atom; and the pharmaceutically acceptable acid addition salts thereof.

In addition, the present invention pertains to a pharmaceutical composition comprising a pharmaceutical carrier and, as an active ingredient, an effective amount of a dibenz [b,e] oxepin derivative represented by the following general formula (I)

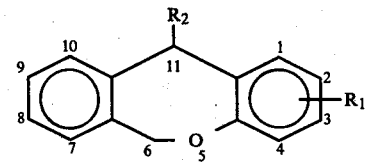

wherein $R_1$ represents an alkyl group containing 1 to 5 carbon atoms, an alkoxy group containing 1 to 5 carbon atoms, a halogen atom, a cyclohexyl group or a phenyl group; and $R_2$ represents

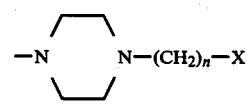

wherein X represents a hydrogen atom, a hydroxy group, an amino group or a substituted aralkyl group containing 7 to 20 carbon atoms, and n has the same meaning as defined before

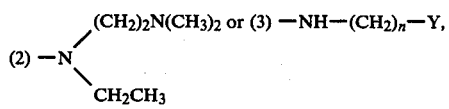

wherein Y and n have the same meaning as defined above; and the pharmaceutically acceptable acid addition salts thereof.

Compound I, represented by the general formula (I) has antichlolinergic, antihistaminergic, antiasthmatic and antiplatelet aggregation activities, and is therefore useful as a sposmolysant, an antihistaminic, an antiasthmatic agent and as a medicament for cardiovascular or cerebrovascular diseases, respectively.

U.S. Pat. No 3,509,176 discloses dibenzo-oxepine derivatives which exhibit muscle-relaxing, transquilizing and anti-convulsant activities. Although not specifically disclosed, compounds 66 to 70 of the present invention are within the scope of the general formula set forth therein.

The present invention is described in detail below.

In compound I and compound Ia, represented by the general formulae (I) and (Ia), respectively, the alkyl group containing 1 to 5 carbon atoms, and represented by $R_1$ and $R_{11}$, includes a methyl group, an ethyl group, a propyl group, a butyl group, an amyl group, etc.

The alkoxy group containing 1 to 5 carbon atoms includes a methoxy group, an ethoxy group, a propoxy group, a butoxy group, a pentoxy group, etc.

The halogen atom includes a fluorine atom, a chlorine atom, a bromine atom, an iodine atom.

The aralkyl group, containing 7 to 20 carbon atoms represented by Y, and the aralkyl group of the substituted aralkyl group containing 7 to 20 carbon atoms, represented by X, includes a benzyl group, a phenylethyl group, a phenylpropyl group, a phenylbutyl group, a diphenylmethyl group, etc. Typical substituted aralkyl groups containing 7 to 20 carbon atoms, and represented by X, include a bis(fluoro-phenyl)methyl group), etc.

The alkylamino group containing 1 to 5 carbon atoms, and represented by Y, includes a methylamino group, an ethylamino group, a propylamino group, a dimethylamino group, a diethylamino group, etc.

The substituent of the aralkyl groups includes halogen atoms such as fluorine and chlorine, alkoxy groups such as methoxy and ethoxy, etc.

The aralkyloxy group containing 7 to 20 carbon atoms includes a benzyloxy group, a diphenylmethoxy group, etc.

The aralkylamino group containing 7 to 20 carbon atoms includes a benzylamino group, a dibenzylamino group, etc.

The heterocyclic ring includes piperazine, piperidine, morpholine, pyrrolidine, pyridine, quinuclidine, benzodioxane, indole, quinoline, etc.

The substituent of the heterocyclic ring includes an alkyl group such as a methyl group, an ethyl group and a propyl group,

The acid addition salts of compound I include inorganic acid addition salts such as hydrochloride, sulfate, hydrobromide, phosphate, etc. and organic acid addition salts such as acetate, maleate, fumarate, tartrate, citrate, oxalate, benzoate, etc.

The present compound can be prepared according to the following processes well known in the field of organic synthesis chemistry using known compound II represented by the following general formula (II):

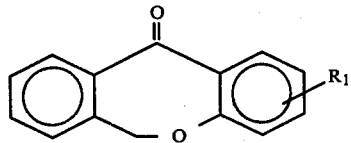

(II)

(wherein R$_1$ has the same meaning as defined above) as intermediates.

Processes for preparing known compound II are described in J. Med. Pharm. Chem., 5, 1207 (1962); Monatsh. Chem., 93, 889 (1962); Angew. Chem., 74, 31 (1962); Belgian Pat. No. 623,259, etc.

For example, the known compound II may be prepared according to the following reaction scheme:

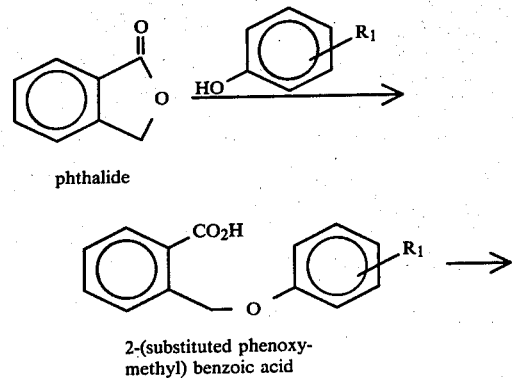

phthalide 2-(substituted phenoxymethyl) benzoic acid

-continued

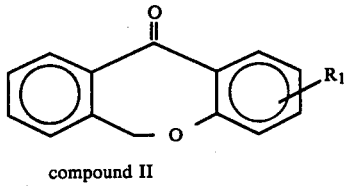

compound II

A typical process for preparing the compounds of the present invention is Process A described below.

Process A

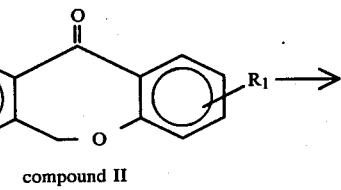

compound II

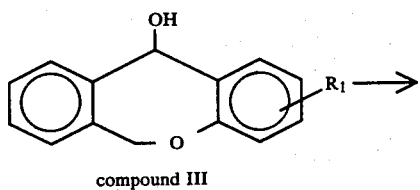

compound III

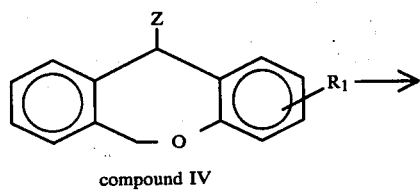

compound IV

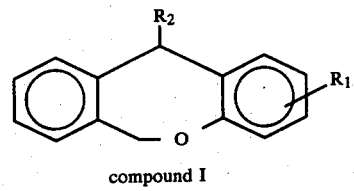

compound I

In the above formulae R$_1$ and R$_2$ have the same meaning as defined above, and Z represents a halogen atom.

Compound II is reduced to compound III, and the resulting compound III is then reacted with a halogenating agent to form compound IV. The compound IV is subsequently reacted with an amine such as

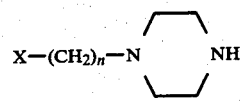

(compound V), Y—(CH$_2$)$_n$—NH$_2$ (compound VI) (wherein X, Y and n have the same meaning as defined before) or

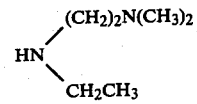

(compound VII) to obtain compound I.

Process A is described in more detail below.

Compound III can be usually obtained by reducing compound II using a metal hydride such as lithium aluminum hydride and sodium borohydride or through catalytic hydrogenation.

In the case of reducing compound II using lithium aluminum hydride, compound II is first dissolved in an anhydrous solvent such as diethyl ether, diisopropyl ether, tetrahydrofuran, diethylene glycol dimethyl ether, or the like, then 0.3 to 2.0 equivalents based on said compound II, of lithium aluminum hydride is added thereto, followed by stirring for 30 minutes to 3 hours at a temperature of from 0° C. to the boiling point of the solvent to complete the reduction. Then, the reaction mixture is post-treated in a conventional manner to obtain compound III.

In the case of reducing compound II using sodium borohydride, compound II is dissolved in a solvent such as water, methanol, ethanol, isopropanol, diethylene glycol dimethyl ether, dimethylformamide, dimethylsulfoxide, or the like, then 0.3 to 1.0 equivalent based on said compound II, of sodium borohydride is added thereto, followed by stirring for one to 8 hours at a temperature of from 0° to 40° C. to complete the reduction. Then, the reaction mixture is post-treated in a conventional manner to obtain compound III.

On the other hand, in the case of reducing compound II according to a catalytic hydrogenation process, compound II is hydrogenated for 2 to 7 hours in a solvent such as methanol, ethanol, dioxane or the like at ordinary temperatures and at atmospheric pressure using a catalyst such as platinum oxide, palladium carbon, Raney nickel, or the like, to obtain compound III. In this procedure the reaction should not be carried out at high temperatures, because it can simultaneously cause hydrogenolysis.

The thus obtained compound III is then converted to compound IV using various halogenating agents. This halogenation can easily be conducted using hydrogen halide, phosphorus halide or thionyl halide as a halogenating agent. Suitable hydrogen halides include concentrated hydrochloric acid, concentrated hydrobromic acid, hydrogen bromide gas, etc. Compound IV can be obtained by reacting compound III with these hydrogen halides per se, or if necessary, in the presence of concentrated sulfuric acid, zinc chloride, pyridine, triethylamine or the like at a temperature of 0° to 60° C. for 30 minutes to 3 hours. Suitable phosphorus halides include phosphorus trichloride, phosphorus pentachloride, phosphorus tribromide, phosphorus pentabromide, phosphorus oxychloride, phosphorus oxybromide, etc. These phosphorus halides are reacted per se in an excess amount with compound III, or in a solvent such as benzene, toluene, xylene, dichloromethane, chloroform, carbon tetrachloride, dimethylformamide, diethyl ether, or the like, at a temperature of 0° to 70° C. for one to 5 hours, if necessary in the presence of a tertiary amine such as pyridine, quinoline, dimethylaniline or triethylamine to obtain compound IV. Suitable thionyl halides include thionyl chloride, thionyl bromide, etc. Compound IV can be obtained according to the same procedure as that using the aforesaid phosphorus halides.

The thus obtained compound IV is then reacted with compound V, VI or VII to obtain compound I. Namely, compound I is prepared by reacting compound IV with 2 to 10 equivalents of compound V, VI or VII, if necessary in an inert solvent such as dichloromethane, chloroform, tetrachloromethane, benzene, toluene, xylene, diethyl ether, diisopropyl ether, tetrahydrofuran, dioxane, n-hexane, cyclohexane, acetonitrile, carbon disulfide, ethyl acetate, dimethylformamide or the like, at a temperature of $-10°$ to 120° C. for 30 minutes to 3 hours. One equivalent of compound V, VI or VII is enough to complete the reaction if a base such as sodium carbonate, sodium hydrogen carbonate, potassium carbonate, potassium hydrogen carbonate, pyridine, quinoline, dimethylaniline or triethylamine is added to the reaction solution in order to bind hydrogen halide as a by-product. The desired compound is obtained as a free base in a crystalline or oily form. If necessary, the desired compound can be further purified through column chromatography or recrystallization.

Acid addition salts of the desired compounds can be easily prepared by reacting the desired compounds with usable inorganic acids such as hydrochloric acid, sulfuric acid, hydrobromic acid and phosphoric acid or organic acids such as acetic acid, maleic acid, fumaric acid, tartaric acid, citric acid, oxalic acid and benzoic acid in a conventional manner.

Furthermore, the present compounds can be also prepared according to the following processes B to E.

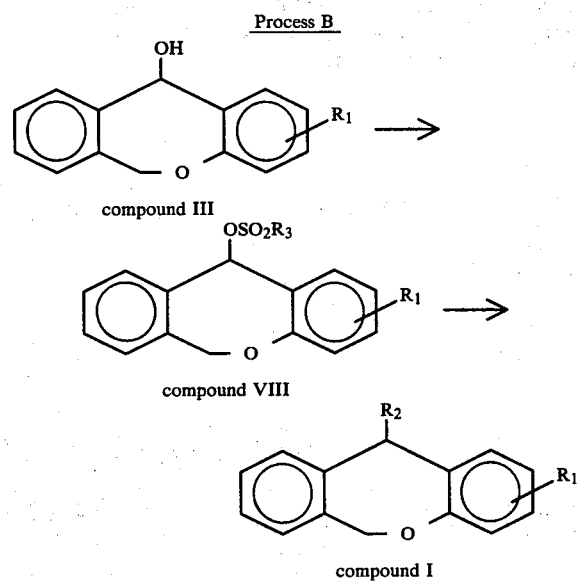

Process B compound III compound VIII compound I

In the above formulae, $R_1$ and $R_2$ have the same meaning as defined above, and $R_3$ represents an alkyl group, a phenyl group or a substituted phenyl group.

The substituted phenyl group includes p-tolyl group, etc.

Compound I can be obtained by reacting compound III obtained by process A with a sulfonylating agent to prepare compound VIII, and then reacting compound VIII with an amine (compound V, VI or VII).

Process C

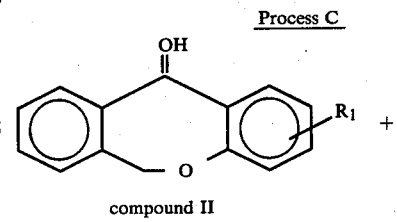

compound II

-continued
Process C

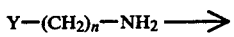

compound VI

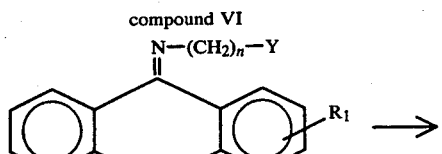

compound IX

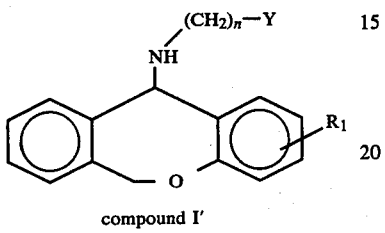

compound I'

In the above formulae, $R_1$, Y, and n have the same meaning as defined above.

Compound I' can be obtained by reducing compound IX prepared by dehydration condensation between compound II and compound VI.

Process D

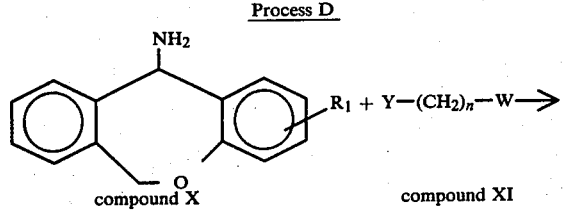

compound X      compound XI

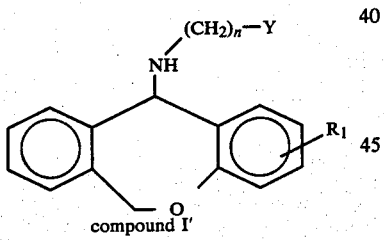

compound I'

In the above formulae, $R_1$, Y, and n have the same meaning as defined above, and W represents a halogen atom or a sulfonyloxy group.

The halogen atom includes a chlorine atom, bromine atom, iodine atom.

The sulfonyloxy group includes a methylsulfonyloxy group, phenylsulfonyloxy group, p-toluenesulfonyloxy group, etc.

Process E

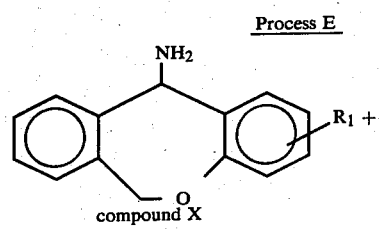

compound X

-continued
Process E

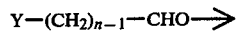

compound XII

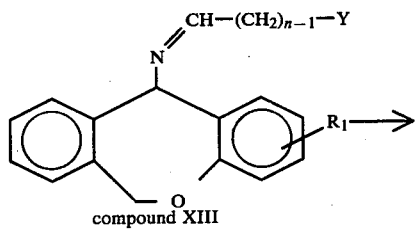

compound XIII

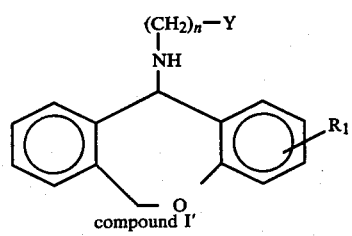

compound I'

In the above formulae, $R_1$ and Y have the same meaning as defined above, and n represents an integer of 1 to 3. Compound I' can be obtained by reducing compound XIII prepared by dehydration condensation between compound X and compound XII.

Typical examples of the present compounds are shown below. The compounds of compound No. (1), (2), ... are hereinafter referred to as compound 1, 2, ..

| Compound No. | Name of Compound |
|---|---|
| (1) | 2-ethyl-11-{2-(diethylamino)ethyl}amino-6,11-dihydrodibenz[b,e]oxepin |
| (2) | 2-ethyl-11-{3-(diethylamino)propyl}amino-6,11-dihydrodibenz[b,e]oxepin |
| (3) | 2-fluoro-11-{3-(diethylamino)propyl}amino-6,11-dihydrodibenz[b,e]oxepin |
| (4) | 2-methyl-11-{3-(diethylamino)propyl}amino-6,11-dihydrodibenz[b,e]oxepin |
| (5) | 2-chloro-11-{3-(diethylamino)propyl}amino-6,11-dihydrodibenz[b,e]oxepin |
| (6) | 4-methyl-11-{3-(diethylamino)propyl}amino-6,11-dihydrodibenz[b,e]oxepin |
| (7) | 2-methoxy-11-{3-(diethylamino)propyl}amino-6,11-dihydrodibenz[b,e]oxepin |
| (8) | 2-methyl-11-{2-(diethylamino)ethyl}amino-6,11-dihydrodibenz[b,e]oxepin |
| (9) | 2-fluoro-11-{2-(diethylamino)ethyl}amino-6,11-dihydrodibenz[b,e]oxepin |
| (10) | 2-chloro-11-{2-(diethylamino)ethyl}amino-6,11-dihydrodibenz[b,e]oxepin |
| (11) | 2-(1-methyl)propyl-11-{2-(diethylamino)ethyl}-amino-6,11-dihydrodibenz[b,e]oxepin |
| (12) | 4-methyl-11-{2-(diethylamino)ethyl}amino-6,11-dihydrodibenz[b,e]oxepin |
| (13) | 2-methoxy-11-{2-(diethylamino)ethyl}amino-6,11-dihydrodibenz[b,e]oxepin |
| (14) | 2-methyl-11-{3-(dimethylamino)propyl}amino-6,11-dihydrodibenz[b,e]oxepin |
| (15) | 2-ethyl-11-{3-(dimethylamino)propyl}amino-6,11-dihydrodibenz[b,e]oxepin |
| (16) | 2-methyl-11-{2-(dimethylamino)ethyl}amino-6,11-dihydrodibenz[b,e]oxepin |
| (17) | 2-ethyl-11-{2-(dimethylamino)ethyl}amino-6,11-dihydrodibenz[b,e]oxepin |
| (18) | 2-fluoro-11-{2-(dimethylamino)ethyl}amino-6,11-dihydrodibenz[b,e]oxepin |
| (19) | 2-chloro-11-{2-(dimethylamino)ethyl}amino-6,11- |

| Compound No. | Name of Compound |
|---|---|
| (20) | 2-methyl-11-(3-quinuclidinyl)amino-6,11-dihydrodibenz[b,e]oxepin |
| (21) | 2-ethyl-11-(3-quinuclidinyl)amino-6,11-dihydrodibenz[b,e]oxepin |
| (22) | 2-fluoro-11-(3-quinuclidinyl)amino-6,11-dihydrodibenz[b,e]oxepin |
| (23) | 2-chloro-11-(3-quinuclidinyl)amino-6,11-dihydrodibenz[b,e]oxepin |
| (24) | 2-methoxy-11-(3-quinuclidinyl)amino-6,11-dihydrodibenz[b,e]oxepin |
| (25) | 2-methyl-11-{2-(1-piperazinyl)ethyl}amino-6,11-dihydrodibenz[b,e]oxepin |
| (26) | 2-ethyl-11-{2-(1-piperazinyl)ethyl}amino-6,11-dihydrodibenz[b,e]oxepin |
| (27) | 2-methyl-11-(1-ethyl-3-piperidyl)amino-6,11-dihydrodibenz[b,e]oxepin |
| (28) | 2-methyl-11-{(1-ethyl-2-pyrrolidinyl)methyl}-amino-6,11-dihydrodibenz[b,e]oxepin |
| (29) | 2-methyl-11-(4-methyl-1-piperazinyl)amino-6,11-dihydrodibenz[b,e]oxepin |
| (30) | 2-fluoro-11-{(1,4-benzodioxane-2-)methyl}amino-6,11-dihydrodibenz[b,e]oxepin |
| (31) | 2-fluoro-11-{bis-(4-fluorophenyl)methyl}amino-6,11-dihydrodibenz[b,e]oxepin |
| (32) | 2-fluoro-11-{(1-methyl-3-phenyl)propyl}amino-6,11-dihydrodibenz[b,e]oxepin |
| (33) | 2-fluoro-11-{2-(diphenylmethyloxy)ethyl}amino-6,11-dihydrodibenz[b,e]oxepin |
| (34) | 2-fluoro-11-{2-(dibenzylamino)ethyl}amino-6,11-dihydrodibenz[b,e]oxepin |
| (35) | 2-ethyl-11-(2-piperidinoethyl)amino-6,11-dihydrodibenz[b,e]oxepin |
| (36) | 2-methyl-11-{2-(2-pyridyl)ethyl}amino-6,11-dihydrodibenz[b,e]oxepin |
| (37) | 2-methyl-11-{4-(2-hydroxyethyl)-1-piperazinyl}-6,11-dihydrodibenz[b,e]oxepin |
| (38) | 2-ethyl-11-{4-(2-hydroxyethyl)-1-piperazinyl}-6,11-dihydrodibenz[b,e]oxepin |
| (39) | 2-fluoro-11-{4-(2-hydroxyethyl)-1-piperazinyl}-6,11-dihydrodibenz[b,e]oxepin |
| (40) | 2-chloro-11-{4-(2-hydroxyethyl)-1-piperazinyl}-6,11-dihydrodibenz[b,e]oxepin |
| (41) | 4-methyl-11-{4-(2-hydroxyethyl)-1-piperazinyl}-6,11-dihydrodibenz[b,e]oxepin |
| (42) | 4-phenyl-11-{4-(2-hydroxyethyl)-1-piperazinyl}-6,11-dihydrodibenz[b,e]oxepin |
| (43) | 2-fluoro-11-[4-{bis-(4-fluorophenyl}methyl-1-piperazinyl]-6,11-dihydrodibenz[b,e]oxepin |
| (44) | 2-methyl-11-{4-(2-aminoethyl)-1-piperazinyl}-6,11-dihydrodibenz[b,e]oxepin |
| (45) | 2-ethyl-11-{4-(2-aminoethyl)-1-piperazinyl}-6,11-dihydrodibenz[b,e]oxepin |
| (46) | 2-fluoro-11-{4-(2-aminoethyl)-1-piperazinyl}-6,11-dihydrodibenz[b,e]oxepin |
| (47) | 4-phenyl-11-(4-methyl-1-piperazinyl)-6,11-dihydrodibenz[b,e]oxepin |
| (48) | 2-cyclohexyl-11-{2-(diethylamino)ethyl}amino-6,11-dihydrodibenz[b,e]oxepin |
| (49) | 2-fluoro-11-(dimethylamino)propyl{amino-6,11-dihydrodibenz[b,e]oxepin |
| (50) | 2-chloro-11-{3-(dimethylamino)propyl}amino-6,11-dihydrodibenz[b,e]oxepin |
| (51) | 2-(1-methyl)propyl-11-(3-quinuclidinyl)amino-6,11-dihydrodibenz[b,e]oxepin |
| (52) | 2-(1,1-dimethyl)ethyl-11-(3-quinuclidinyl)amino-6,11-dihydrodibenz[b,e]oxepin |
| (53) | 2-(1,1-dimethyl)propyl-11-(3-quinuclidinyl)amino-6,11-dihydrodibenz[b,e]oxepin |
| (54) | 2-cyclohexyl-11-(3-quinuclidinyl)amino-6,11-dihydrodibenz[b,e]oxepin |
| (55) | 2-phenyl-11-(3-quinuclidinyl)amino-6,11-dihydrodibenz[b,e]oxepin |
| (56) | 4-methyl-11-(3-quinuclidinyl)amino-6,11-dihydrodibenz[b,e]oxepin |
| (57) | 4-phenyl-11-(3-quinuclidinyl)amino-6,11-dihydrodibenz[b,e]oxepin |
| (58) | 2-methyl-11-{2-(1-pyrrolidinyl)ethyl}amino-6,11-dihydrodibenz[b,e]oxepin |
| (59) | 2-methyl-11-(2-morpholinoethyl)amino-6,11-dihydrodibenz[b,e]oxepin |
| (60) | 2-fluoro-11-{2-(3,4-dimethoxyphenyl)ethyl}amino-6,11-dihydrodibenz[b,e]oxepin |
| (61) | 2-ethyl-11-(5-quinolyl)amino-6,11-dihydrodibenz[b,e]oxepin |
| (62) | 2-methyl-11-(5-indolyl)amino-6,11-dihydrodibenz[b,e]oxepin |
| (63) | 2-ethyl-11-{4-(2,2,6,6-tetramethyl)piperidinyl}-amino-6,11-dihydrodibenz[b,e]oxepin |
| (64) | 2-methyl-11-[N—{2-(dimethylamino)ethyl}-N—ethyl]-amino-6,11-dihydrodibenz[b,e]oxepin |
| (65) | 2-methyl-11-(1',3'-dioxoran-2'-spiro-4-piperidino)-6,11-dihydrodibenz[b,e]oxepin |
| (66) | 2-ethyl-11-(4-methyl-1-piperazinyl)-6,11-dihydrodibenz[b,e]oxepin |
| (67) | 2-methyl-11-(4-methyl-1-piperazinyl)-6,11-dihydrodibenz[b,e]oxepin |
| (68) | 2-methoxy-11-(4-methyl-1-piperazinyl)-6,11-dihydrodibenz[b,e]oxepin |
| (69) | 2-fluoro-11-(4-methyl-1-piperazinyl)-6,11-dihydrodibenz[b,e]oxepin |
| (70) | 2-chloro-11-(4-methyl-1-piperazinyl)-6,11-dihydrodibenz[b,e]oxepin |

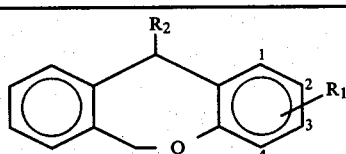

(I)

| Compound No. | Position of $R_1$ | $R_1$ | $R_2$ |
|---|---|---|---|
| (1) | 2 | —CH$_2$CH$_3$ | —NH(CH$_2$)$_2$N(CH$_2$CH$_3$)$_2$ |
| (2) | 2 | " | —NH(CH$_2$)$_3$N(CH$_2$CH$_3$)$_2$ |
| (3) | 2 | —F | " |
| (4) | 2 | —CH$_3$ | " |
| (5) | 2 | —Cl | " |
| (6) | 4 | —CH$_3$ | " |
| (7) | 2 | —OCH$_3$ | " |
| (8) | 2 | —CH$_3$ | —NH(CH$_2$)$_2$N(CH$_2$CH$_3$)$_2$ |
| (9) | 2 | —F | " |
| (10) | 2 | —Cl | " |
| (11) | 2 | —CH(CH$_3$)CH$_2$CH$_3$ | " |
| (12) | 4 | —CH$_3$ | " |
| (13) | 2 | —OCH$_3$ | " |
| (14) | 2 | —CH$_3$ | —NH(CH$_2$)$_3$N(CH$_3$)$_2$ |

-continued
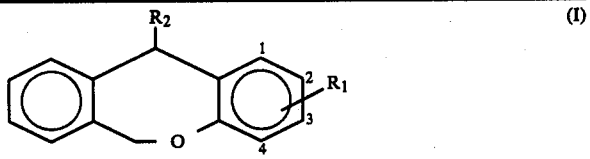
(I)
| Compound No. | Position of R₁ | R₁ | R₂ |
|---|---|---|---|
| (15) | 2 | —CH₂CH₃ | ″ |
| (16) | 2 | —CH₃ | —NH(Ch₂)₂N(CH₃)₂ |
| (17) | 2 | —CH₂CH₃ | ″ |
| (18) | 2 | —F | ″ |
| (19) | 2 | —Cl | ″ |
| (20) | 2 | —CH₃ | —NH—[3-quinuclidinyl] |
| (21) | 2 | —CH₂CH₃ | ″ |
| (22) | 2 | —F | ″ |
| (23) | 2 | —Cl | ″ |
| (24) | 2 | —OCH₃ | ″ |
| (25) | 2 | —CH₃ | —NH(CH₂)₂N[piperazinyl]NH |
| (26) | 2 | —CH₂CH₃ | ″ |
| (27) | 2 | —CH₃ | —NH—[1-ethyl-3-piperidinyl] |
| (28) | 2 | —CH₃ | —NHCH₂—[1-ethyl-2-piperidinyl] |
| (29) | 2 | —CH₃ | —NH—N[piperazinyl]NCH₃ |
| (30) | 2 | —F | —NHCH₂—[1,4-benzodioxan-2-yl] |
| (31) | 2 | —F | —NHCH(—C₆H₄—F)₂ |
| (32) | 2 | —F | —NHCH(CH₃)CH₂CH₂—C₆H₅ |
| (33) | 2 | —F | —NH(CH₂)₂—O—CH(—C₆H₅)₂ |

-continued $$(I)$$

[Structure of formula (I): dibenzoxepine-type tricyclic system with R₂ substituent on the methine carbon and R₁ substituent on the aromatic ring at positions 1, 2, 3, or 4]

| Compound No. | Position of R₁ | R₁ | R₂ |
|---|---|---|---|
| (34) | 2 | —F | —NH(CH₂)₂N(—CH₂—cyclohexyl)₂ |
| (35) | 2 | —CH₂CH₃ | —NH(CH₂)₂N(piperidinyl) |
| (36) | 2 | —CH₃ | —NH(CH₂)₂-(2-pyridyl) |
| (37) | 2 | —CH₃ | —N(piperazinyl)N(CH₂)₂OH |
| (38) | 2 | —CH₂CH₃ | " |
| (39) | 2 | —F | " |
| (40) | 2 | —Cl | " |
| (41) | 4 | —CH₃ | " |
| (42) | 4 | —C₆H₅ (phenyl) | " |
| (43) | 2 | —F | —N(piperazinyl)N—CH(-4-F-C₆H₄)₂ |
| (44) | 2 | —CH₃ | —N(piperazinyl)N(CH₂)₂NH₂ |
| (45) | 2 | —CH₂CH₃ | " |
| (46) | 2 | —F | " |
| (47) | 4 | —C₆H₅ (phenyl) | —N(piperazinyl)NCH₃ |
| (48) | 2 | —C₆H₁₁ (cyclohexyl) | —NH(CH₂)₂N(C₂H₅)₂ |
| (49) | 2 | —F | —NH(CH₂)₃N(CH₃)₂ |
| (50) | 2 | —Cl | " |
| (51) | 2 | —CH(CH₃)CH₂CH₃ | —NH-(quinuclidin-3-yl) |

-continued
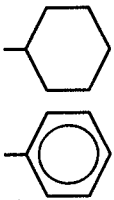
| Compound No. | Position of R₁ | R₁ | R₂ |
|---|---|---|---|
| (52) | 2 | —C(CH₃)₃ | " |
| (53) | 2 | —C(CH₃)₂CH₂CH₃ | " |
| (54) | 2 |  | " |
| (55) | 2 | 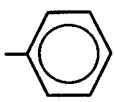 | " |
| (56) | 4 | —CH₃ | " |
| (57) | 4 | 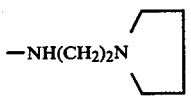 | " |
| (58) | 2 | —CH₃ | —NH(CH₂)₂N⟨pyrrolidine⟩ |
| (59) | 2 | —CH₃ | —NH(CH₂)₂N⟨morpholine⟩ |
| (60) | 2 | F | 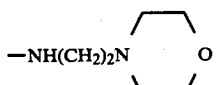 |
| (61) | 2 | —CH₂CH₃ | 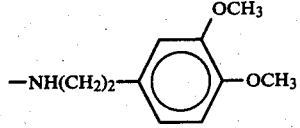 |
| (62) | 2 | —CH₃ | 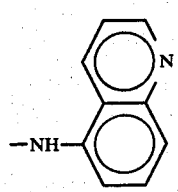 |
| (63) | 2 | —CH₂CH₃ | 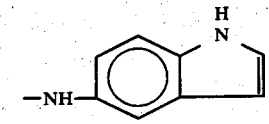 |

-continued $$\text{(I)}$$

[Structure: isochroman/chromene-type bicyclic with R₂ on benzylic carbon, R₁ on aromatic ring positions 1,2,3,4]

| Compound No. | Position of R₁ | R₁ | R₂ |
|---|---|---|---|
| (64) | 2 | —CH₃ | —N(CH₂)₂N(CH₃)₂ / CH₂CH₃ |
| (65) | 2 | —CH₃ | —N(morpholine-like with two O) |
| (66) | 2 | —C₂H₅ | —N␣␣␣N—CH₃ (N-methylpiperazine) |
| (67) | 2 | —CH₃ | " |
| (68) | 2 | —OCH₃ | " |
| (69) | 2 | —F | " |
| (70) | 2 | —Cl | —N␣␣␣N—CH₃ |

The pharmacological activity of the compound I represented by the general formula (I) is illustrated in (a) an acute toxicity test, (b) a test for anticholinergic effects on the isolated ileum of a guinea-pig, (c) a test for antihistaminergic effects on the isolated ileum of a guinea-pig, and (d) a test for the inhibition of platelet aggregation. Each of these tests is described in detail below.

(a) Acute toxicity test

Groups of male dd-strain rats (each group consisting of five rats) weighing 20±1 g were used. The compounds of the present invention were administered orally (po: 0.3 mg/g) or intraperitoneally (ip: 0.1 mg/g). The MLD (minimum lethal dose) was calculated from the mortality for 7 days after the administration to obtain the results given in Table 1.

(b) Test for anticholinergic effects on the isolated ileum of guinea-pig (In vitro test)

Male Hartly-strain guinea-pigs weighing about 250 g are killed and the abdomen is opened. The part (2–3 cm in length) of the ileum 10 cm away from the caecum to the pylorus is cut off as a preparation. The preparation is suspended with serre-fine in a Magnus bath containing 10 ml of Tyrode's solution at 32°±1° C. under an air bubble. The contraction of the ileum is recorded on Kymograph through hebel when 0.1 ml of acetylcholine at a concentration of $10^{-3}$ g/ml is added to the Tyrode's solution.

On the other hand, 3 minutes after administration of the test compounds, the same procedure as mentioned above is carried out to record the contraction. The test compounds showing a depressing ratio of 80% or more, compared with the concentration of the ileum by acetylcholine alone, are concluded to have anticholingenergic activity. A final concentration of the test compounds is reduced until the depressing ratio is less than 80% to obtain the minimum effective dose (hereinafter referred to as MED). The results are shown in Table 1.

(c) Test for antihistaminergic effects on the isolated ileum of guinea-pig (In vitro test)

In this test, 0.1 ml of histamine at a concentration of $5 \times 10^{-3}$ g/l is used. The MED exhibiting antihistaminergic activity is obtained by a procedure similar to that used to determine the anticholinergic effect as described above. The results are shown in Table 1.

(d) Test for the inhibition of platelet aggregation

In this test, 9 vols. of blood are sampled from the caroted artery of male white rabbits weighing 2 to 2.5 kg and placed in a silicon-coated flask containing 1 vol. of 3.8% sodium citrate. The thus obtained blood is centrifuged at 1,000 rpm for 15 minutes to obtain platelet-rich plasma. The aggregation of the blood platelets is observed using an aggregometer, when collagen is added to the platelet-rich plasma to the extent of the final concentration that 50% of platelet aggregation is caused in the presence of 100 γ/ml of aspirin. On the other hand, 3 minutes after administration of the test compounds to the platelet-rich plasma, the same procedure as mentioned above is carried out to observe the aggregation of blood platelet. The test compounds showing a depressing ratio of 50%, compared with the inhibition of aggregation by collagen alone, are concluded to have antiplatelet aggregation activity. A final concentration of the test compounds is reduced until the depressing ratio is less than 50% to obtain MED exhibiting antiplatelet aggregation activity. The results are shown in Table 1.

TABLE 1

| Compound | Acute toxicity: MLD (mg/kg) po | Acute toxicity: MLD (mg/kg) ip | Antichloinergic activity: MED (γ/ml) | Antihistaminergic activity: MED (γ/ml) | Antiplatelet aggregation activity: MED (γ/ml) | Antiasthmatic activity: MED (mg/kg po) |
|---|---|---|---|---|---|---|
| 1 | >300 | >100 | 1 | 1 | 20 | 50 |
| 2 | 300 | 100 | 10 | 1 | 1 | — |
| 3 | >300 | >100 | 10 | 10 | 20 | — |
| 4 | 300 | 100 | 10 | 10 | 20 | — |
| 5 | 300 | >100 | 1 | 1 | 20 | — |
| 6 | 300 | 100 | 3 | 10 | 20 | — |
| 7 | >300 | 100 | 0.3 | 0.3 | — | — |
| 8 | 200 | >100 | 10 | 1 | 20 | 25 |
| 9 | >300 | 100 | 3 | 1 | 50 | 50 |
| 10 | >300 | >100 | — | — | 2 | 100 |
| 11 | >300 | 100 | 0.03 | 0.3 | 10 | 100 |
| 12 | >300 | 100 | — | — | 10 | — |
| 13 | >300 | >100 | 1 | 0.3 | 20 | 100 |
| 14 | >300 | >100 | 10 | 10 | 20 | 100 |
| 15 | >300 | >100 | 3 | 3 | 20 | — |
| 16 | 300 | >100 | 3 | 10 | 50 | 25 |
| 17 | 300 | >100 | 0.01 | 0.3 | 50 | 10 |
| 18 | >300 | >100 | 0.3 | 0.3 | 50 | 10 |
| 19 | >300 | >100 | 3 | 1 | 50 | 25 |
| 20 | 300 | 50 | 1 | 0.1 | 100 | 50 |
| 21 | 300 | 100 | 0.1 | 0.1 | 50 | 25 |
| 22 | 300 | 100 | 0.3 | 0.3 | 100 | 50 |
| 23 | 300 | 100 | 1 | 0.3 | 100 | 50 |
| 24 | 200 | 100 | 0.3 | 0.1 | 100 | 50 |
| 25 | >300 | >100 | 10 | 10 | 20 | — |
| 26 | >300 | >100 | 3 | 3 | 5 | — |
| 27 | 300 | >100 | 1 | 10 | 100 | — |
| 28 | 300 | 100 | 1 | 1 | 50 | 25 |
| 29 | >300 | >100 | — | 10 | 50 | — |
| 30 | >300 | >100 | 10 | 10 | — | — |
| 31 | >300 | >100 | — | — | 100 | — |
| 32 | >300 | >100 | 3 | — | — | — |
| 33 | >300 | >100 | — | — | 100 | — |
| 34 | 300 | >100 | — | 10 | — | — |
| 35 | 300 | >100 | 3 | 1 | 20 | 25 |
| 36 | 200 | 100 | 10 | 3 | 100 | — |
| 37 | >300 | >100 | 10 | 10 | 50 | — |
| 38 | >300 | >100 | 1 | 1 | 100 | 100 |
| 39 | >300 | 100 | 1 | 10 | 50 | 100 |
| 40 | >300 | >100 | — | 3 | 100 | 50 |
| 41 | >300 | >100 | — | — | 100 | — |
| 42 | >300 | >100 | — | — | 100 | — |
| 43 | >300 | >100 | — | — | 100 | — |
| 44 | >300 | 100 | 10 | 10 | — | — |
| 45 | >300 | 100 | 10 | 10 | 100 | — |
| 46 | >300 | >100 | — | 1 | 50 | — |
| 47 | 200 | 100 | 3 | 10 | 10 | — |
| 48 | >300 | 100 | 3 | 3 | 100 | — |
| 49 | >300 | >100 | 3 | 1 | 50 | — |
| 50 | 200 | >100 | 10 | 3 | 50 | — |
| 51 | >300 | 100 | 1 | 0.3 | 50 | 50 |
| 52 | >300 | 100 | 3 | 0.3 | 1 | 50 |
| 53 | >300 | 50 | 10 | 1 | — | 50 |
| 54 | >300 | 100 | 10 | 1 | — | — |
| 55 | >300 | >100 | 3 | 1 | 20 | — |
| 56 | 200 | 100 | 1 | 1 | 20 | 100 |
| 57 | >300 | 100 | 3 | 3 | 10 | — |
| 58 | 300 | >100 | 3 | 0.1 | 50 | 25 |
| 59 | 200 | >100 | — | 10 | 100 | 100 |
| 60 | >300 | >100 | — | 10 | — | — |
| 61 | >300 | >100 | — | 10 | — | — |
| 62 | >300 | >100 | — | — | 50 | — |
| 63 | 200 | 100 | 3 | 3 | 10 | — |
| 64 | >300 | >100 | 10 | 10 | — | — |
| 65 | >300 | >100 | — | 10 | — | — |
| 66 | >300 | >100 | 10 | 1 | 50 | 10 |
| 67 | >300 | >100 | 10 | 0.3 | 50 | 25 |
| 68 | 200 | 100 | 10 | 3 | 100 | 100 |
| 69 | 100 | >100 | 3 | 10 | 100 | 100 |
| 70 | 200 | 100 | 1 | 0.3 | 50 | 10 |

As is apparent from Table 1, the present compounds have anticholinergic, antihistaminergic, antiasthmatic and antiplatelet aggregation activities. The compounds as such are useful as a sposmolysant, an antihistaminic, an antiasthmatic agent and as a medicament for cardiovascular or cerebrovascular diseases.

In view of the exhibited pharmacological activity, a compound represented by the general formula (I) may be used in various pharmaceutical forms for administration. Pharmaceutical compositions of the present invention are prepared by uniformly mixing an effective amount of the compound as the active ingredient, in free form or as an acid addition, salt, with a pharmaceutically acceptable carrier. The carrier may take various forms depending on the pharmaceutical form suitable for administration. It is preferable that the pharmaceutical composition is in single administration form suitable for administration orally or by injection.

To prepare the compositions of the present invention for oral administration, any useful pharmaceutical carrier may be used. For example, oral liquid preparations such as suspensions and syrups can be prepared using water, sugar (e.g. sucrose, sorbitol and fructose), glycols (e.g. polyethyleneglycol and propyleneglycol), oils (e.g. sesame oil, olive oil and soybean oil), antisepics (e.g. alkyl parahydroxybenzoate and dehydroacetic acid), flavours (e.g. strawberry flavour and peppermint) and the like. Powders, pills, capsules and tablets can be prepared using excipients (e.g. lactose, glucose, sucrose and mannitol), disintegrators (e.g. starch, sodium alginate and carboxymethyl cellulose calcium), lubricants (e.g. magnesium stearate and talc), binders (e.g. polyvinyl alcohol, hydroxypropylcellulose, and gelatin), surfactants (e.g sucrose fatty acid ester and sorbitan fatty acid ester), plasticizers (e.g. glycerin) and the like.

Tablets and capsules are the most useful single oral administration forms because of the ease of administration. To make tablets and capsules solid pharmaceutical carriers are used.

Where pharmaceutical compositions for parenteral administration are desired, the carrier for the most part consists of sterile aqueous solutions. The carrier, however, may also contain other components to help the dissolution of the dibenz [b,e] oxepin derivatives.

For example, an injection solution can be prepared using a carrier consisting of a mixture of salt solution and glucose solution or saline solution and glucose solution.

The suspensions for injection can be prepared using an appropriate liquid carrier, dispensing agent and the like. Although the amount of the active ingredient can be varied over a rather wide range, 1–20 mg/kg/day in one dose or several divided doses is generally considered to be effective.

Certain specific embodiments of the invention are illustrated by the following representative examples.

EXAMPLE 1

Preparation of compound 1

2-ethyl-11-[2-(diethylamino)ethyl]amino-6,11-dihydrodibenz [b,d] oxepin

In this example, 4.8 g of 2-ethyl-6,11-dihydrodibenz [b,e] oxepinone-11 is dissolved in 30 ml of ethanol, and 0.4 g of sodium borohydride is added thereto, followed by stirring at room temperature for 5 hours. The reaction solution is concentrated under reduced pressure to distill off ethanol. Then, 20 ml of water and 20 ml of chloroform are added to the residue and after shaking, an aqueous layer is discarded. A chloroform layer is dehydrated and concentrated under reduced pressure to obtain 4.8 g of crude crystals of 2-ethyl-11-hydroxy-6,11-dihydrodibenz [b,e] oxepin. Recrystallizatin of the crude crystals from 50 ml of n-hexane gives 4.6 g of pure crystals in a yield of 96%. The resulting crystals are dissolved in 20 ml of dichloromethane, and 4.6 g of thionyl chloride is dropwise added thereto for 15 minutes. After completion of the dropwise addition, the resulting mixture is stirred for 30 minutes at room temperature. The reaction solution is concentrated under reduced pressure to distill off dichloromethane and excess thionyl chloride. Thus, 5.0 g of crude crystals of 2-ethyl-11-chloro-6,11-dihydrodibenz [b,e] oxepin are obtained as a concentrated residue.

The crude product is dissolved in 10 ml of toluene and added dropwise to a solution of 4.0 g of N,N-diethylethylenediamine in 20 ml of toluene, followed by stirring for 3 hours at room temperature. After completion of the reaction, 20 ml of water is added thereto, and the pH of the solution is adjusted to 2.0 with concentrated hydrochloric acid. A toluene layer was discarded, and 20 ml of ethyl ether is added to an aqueous layer, followed by readjusting the pH of the solution to 10.5 with a 10 N sodium hydroxide aqueous solution. An aqueous layer is discarded, and an ethyl ether layer is dehydrated and concentrated under reduced pressure. The residue is purified through silica gel chromatography. Concentration of the main fractions gives 4.9 g of 2-ethyl-11-[2-(diethylamino)ethyl] amino-6,11-dihydrodibenz [b,e] oxepin [compound 1] in an oily free base in a yield of 76%. This product is dissolved in 150 ml of ethyl ether, and a hydrogen chloride gas is blown thereinto a obtain 5.1 g of dihydrochloride crystals.

m.p.: (the dihydrochloride is too phgroscopic to measure).

IR absorption spectrum (NaCl cell, $cm^{-1}$): 2970, 1500, 1230, 1125, 1015, 825.

NMR spectrum ($CDCl_3$, $\delta$ value, ppm): 0.94(t, 6H), 1.18(t, 3H), 2.03–3.07(m, 11H), 4.52(s, 1H), 4.81(d, 1H), 6.17(d, 1H), 6.60–7.57 (m, 7H).

Elemental analysis of dihydrochloride:

|  | C (%) | H (%) | N (%) |
|---|---|---|---|
| Calcd. for $C_{22}H_{32}Cl_2N_2O$: | 64.22 | 7.84 | 6.81 |
| Found: | 63.99 | 8.02 | 7.02 |

EXAMPLES 2 TO 36

Compounds 2 to 36 and Compounds 48 to 70 mentioned below are obtained in a similar manner to that in Example 1 except that Compound II shown in Table 2 and amine are used in stead of 2-ethyl-6,11-dihydrodibenz [b,e] oxepine-11 (Compound II) and N,N-diethylethylenediamine in Example 1.

TABLE 2

| Example | Compound II name | used amount (g) | Amine name | used amount (g) | Obtained amount of the desired compound (g) |
|---|---|---|---|---|---|
| 2 | 2-ethyl-6,11-dihydrodibenz [b,e]oxepinone-11 | 2.4 | N,N—diethyl-1,3-propandiamine | 3.5 | 2.6 |
| 3 | 2-fluoro-6,11-dihydrodibenz [b,e]oxepinone-11 | 2.3 | N,N—diethyl-1,3-propandiamine | 2.6 | 2.4 |

TABLE 2-continued

| Example | Compound II name | used amount (g) | Amine name | used amount (g) | Obtained amount of the desired compound (g) |
|---|---|---|---|---|---|
| 4 | 2-methyl-6,11-dihydrodibenz[b,e]oxepinone-11 | 2.2 | N,N—diethyl-1,3-propandiamine | 2.6 | 2.5 |
| 5 | 2-chloro-6,11-dihydrodibenz[b,e]oxepinone-11 | 2.4 | N,N—diethyl-1,3-propandiamine | 2.6 | 2.7 |
| 6 | 4-methyl-6,11-dihydrodibenz[b,e]oxepinone-11 | 2.2 | N,N—diethyl-1,3-propandiamine | 2.6 | 2.8 |
| 7 | 2-methoxy-6,11-dihydrodibenz[b,e]oxepinone-11 | 2.4 | N,N—diethyl-1,3-propandiamine | 2.6 | 3.0 |
| 8 | 2-methyl-6,11-dihydrodibenz[b,e]oxepinone-11 | 3.4 | N,N—diethylethylenediamine | 5.8 | 3.6 |
| 9 | 2-fluoro-6,11-dihydrodibenz[b,e]oxepinone-11 | 2.3 | N,N—diethylethylenediamine | 2.4 | 2.3 |
| 10 | 2-chloro-6,11-dihydrodibenz[b,e]oxepinone-11 | 2.4 | N,N—diethylethylenediamine | 2.3 | 2.4 |
| 11 | 2-(1-methyl)propyl-6,11-dihydrodibenz[b,e]oxepinone-11 | 2.7 | N,N—diethylethylenediamine | 2.3 | 2.6 |
| 12 | 4-methyl-6,11-dihydrodibenz[b,e]oxepinone-11 | 3.4 | N,N—diethylethylenediamine | 4.6 | 4.2 |
| 13 | 2-methoxy-6,11-dihydrodibenz[b,e]oxepinone-11 | 2.4 | N,N—diethylethylenediamine | 2.3 | 2.5 |
| 14 | 2-methyl-6,11-dihydrodibenz[b,e]oxepinone-11 | 2.2 | N,N—dimethyl-1,3-propandiamine | 2.0 | 2.4 |
| 15 | 2-ethyl-6,11-dihydrodibenz[b,e]oxepinone-11 | 2.4 | N,N—dimethyl-1,3-propandiamine | 2.0 | 2.6 |
| 16 | 2-methyl-6,11-dihydrodibenz[b,e]oxepinone-11 | 2.2 | N,N—dimethylethylenediamine | 1.8 | 2.3 |
| 17 | 2-ethyl-6,11-dihydrodibenz[b,e]oxepinone-11 | 2.4 | N,N—dimethylethylenediamine | 1.8 | 2.4 |
| 18 | 2-fluoro-6,11-dihydrodibenz[b,e]oxepinone-11 | 2.3 | N,N—dimethylethylenediamine | 1.8 | 2.4 |
| 19 | 2-chloro-6,11-dihydrodibenz[b,e]oxepinone-11 | 2.4 | N,N—dimethylethylenediamine | 1.8 | 2.6 |
| 20 | 2-methyl-6,11-dihydrodibenz[b,e]oxepinone-11 | 2.2 | 3-aminoquinuclidine | 2.5 | 2.5 |
| 21 | 2-ethyl-6,11-dihydrodibenz[b,e]oxepinone-11 | 2.4 | " | 2.5 | 2.7 |
| 22 | 2-fluoro-6,11-dihydrodibenz[b,e]oxepinone-11 | 2.3 | " | 2.5 | 2.1 |
| 23 | 2-chloro-6,11-dihydrodibenz[b,e]oxepinone-11 | 2.4 | " | 2.5 | 1.9 |
| 24 | 2-methoxy-6,11-dihydrodibenz[b,e]oxepinone-11 | 2.4 | " | 2.5 | 2.4 |
| 25 | 2-methyl-6,11-dihydrodibenz[b,e]oxepinone-11 | 4.4 | N—(2-aminoethyl)piperazine | 5.2 | 1.2 |
| 26 | 2-ethyl-6,11-dihydrodibenz[b,e]oxepinone-11 | 4.8 | N—(2-aminoethyl)piperazine | 5.2 | 2.3 |
| 27 | 2-methyl-6,11-dihydrodibenz[b,e]oxepinone-11 | 2.2 | 1-ethyl-3-aminopiperidine | 2.6 | 2.4 |
| 28 | 2-methyl-6,11-dihydrodibenz[b,e]oxepinone-11 | 2.2 | 1-ethyl-2-aminomethylpyrrolidine | 2.6 | 2.3 |
| 29 | 2-methyl-6,11-dihydrodibenz[b,e]oxepinone-11 | 2.2 | 1-amino-4-methylpiperazine | 2.3 | 2.2 |
| 30 | 2-fluoro-6,11-dihydrodibenz[b,e]oxepinone-11 | 4.6 | 2-aminoethyl-1,4-benzodioxane | 4.0 | 3.2 |
| 31 | 2-fluoro-6,11-dihydrodibenz[b,e]oxepinone-11 | 4.6 | {bis-(4-fluorophenyl)}-methylamine | 4.5 | 4.1 |
| 32 | 2-fluoro-6,11-dihydrodibenz[b,e]oxepinone-11 | 4.6 | 1-phenyl-3-aminobutane | 3.2 | 4.2 |
| 33 | 2-fluoro-6,11-dihydrodibenz[b,e]oxepinone-11 | 4.6 | 2-diphenylmethyloxyethylamine | 4.7 | 4.5 |
| 34 | 2-fluoro-6,11-dihydrodibenz[b,e]oxepinone-11 | 4.6 | 2-dibenzylaminoethylamine | 5.0 | 3.0 |
| 35 | 2-ethyl-6,11-dihydrodibenz[b,e]oxepinone-11 | 2.4 | N—(2-aminoethyl)piperidine | 2.6 | 2.7 |
| 36 | 2-methyl-6,11-dihydrodibenz[b,e]oxepinone-11 | 2.2 | 2-(2-aminoethyl)pyridine | 2.4 | 2.4 |
| 48 | 2-cyclohexyl-6,11-dihydrodibenz[b,e]oxepinone-11 | 2.9 | N,N-diethylethylenediamine | 2.3 | 2.8 |
| 49 | 2-fluoro-6,11-dihydrodibenz[b,e]oxepinone-11 | 2.3 | N,N—dimethyl-1,3-propanediamine | 2.0 | 2.2 |
| 50 | 2-chloro-6,11-dihydrodibenz[b,e]oxepinone-11 | 2.4 | N,N—dimethyl-1,3-propanediamine | 2.0 | 2.5 |
| 51 | 2-(1-methyl)propyl-6,11-dihydrodibenz[b,e]oxepinone-11 | 2.7 | 3-aminoquinuclidine | 2.5 | 2.6 |
| 52 | 2-(1,1-dimethyl)ethyl-6,11-dihydrodibenz[b,e]oxepinone-11 | 2.7 | " | 2.5 | 2.5 |
| 53 | 2-(1,1-dimethyl)propyl-6,11- | 2.8 | " | 2.5 | 2.6 |

TABLE 2-continued

| Example | Compound II name | used amount (g) | Amine name | used amount (g) | Obtained amount of the desired compound (g) |
|---|---|---|---|---|---|
| | dihydrodibenz[b,e]oxepinone-11 | | | | |
| 54 | 2-cyclohexyl-6,11-dihydro-dibenz[b,e]oxepinone-11 | 2.9 | " | 2.5 | 2.8 |
| 55 | 2-phenyl-6,11-dihydrodibenz[b,e]oxepinone-11 | 2.9 | " | 2.5 | 2.8 |
| 56 | 4-methyl-6,11-dihydrodibenz[b,e]oxepinone-11 | 2.2 | " | 2.5 | 2.3 |
| 57 | 4-phenyl-6,11-dihydrodibenz[b,e]oxepinone-11 | 2.9 | " | 2.5 | 2.6 |
| 58 | 2-methyl-6,11-dihydrodibenz[b,e]oxepinone-11 | 2.2 | N—(2-aminoethyl)pyrrolidine | 2.2 | 2.4 |
| 59 | 2-methyl-6,11-dihydrodibenz[b,e]oxepinone-11 | 2.2 | N—(2-aminoethyl)morpholine | 2.6 | 2.6 |
| 60 | 2-fluoro-6,11-dihydrodibenz[b,e]oxepinone-11 | 2.3 | 2-(3,4-dimethoxyphenyl)-ethylamine | 3.6 | 2.2 |
| 61 | 2-ethyl-6,11-dihydrodibenz[b,e]oxepinone-11 | 2.4 | 5-aminoquinoline | 2.8 | 2.4 |
| 62 | 2-methyl-6,11-dihydrodibenz[b,e]oxepinone-11 | 2.2 | 5-aminoindole | 2.6 | 1.9 |
| 63 | 2-ethyl-6,11-dihydrodibenz[b,e]oxepinone-11 | 2.4 | 4-amino-2,2,6,6-tetramethylpiperidine | 3.1 | 2.3 |
| 64 | 2-methyl-6,11-dihydrodibenz[b,e]oxepinone-11 | 2.2 | N,N—dimethyl-N'—ethyl-ethylenediamine | 2.3 | 2.5 |
| 65 | 2-methyl-6,11-dihydrodibenz[b,e]oxepinone-11 | 2.2 | 4-piperidone ethylene acetal | 2.9 | 2.3 |
| 66 | 2-ethyl-6,11-dihydrodibenz[b,e]oxepinone-11 | 4.8 | 1-methylpiperazine | 9.6 | 3.2 |
| 67 | 2-methyl-6,11-dihydrodibenz[b,e]oxepinone-11 | 4.5 | " | 4.8 | 3.0 |
| 68 | 2-methoxy-6,11-dihydrodibenz[b,e]oxepinone-11 | 4.8 | " | 2.2 | 4.0 |
| 69 | 2-fluoro-6,11-dihydrodibenz[b,e]oxepinone-11 | 4.6 | " | 4.4 | 3.7 |
| 70 | 2-chloro-6,11-dihydrodibenz[b,e]oxepinone-11 | 4.0 | " | 4.4 | 4.0 |

Compound 2

2-ethyl-11-{3-(diethylamino)propyl}amino-6,11-dihydrodibenz [b,e] oxepin m.p.: (dihydrochloride being too hygroscopic to measure).

IR absorption spectrum (NaCl cell, cm$^{-1}$): 2970, 1500, 1380, 1230, 1020, 830.

NMR spectrum (CDCl$_3$, δ value, ppm): 0.94(t, 6H), 1.19(t, 3H), 0.71–1.88(m, 2H), 2.14–2.88(m, 11H), 4.50(s, 1H), 4.78(d, 1H), 6.21(d, 1H), 6.68–7.48(m, 7H).

Elemental analysis of dihydrochloride:

| | C (%) | H (%) | N (%) |
|---|---|---|---|
| Calcd. for C$_{23}$H$_{34}$Cl$_2$N$_2$O: | 64.93 | 8.06 | 6.58 |
| Found: | 65.00 | 8.04 | 6.81 |

Compound 3

2-fluoro-11-{3-diethylamino)propyl}amino-6,11-dihydrodibenz [b,e] oxepin m.p.: (dihydrochloride being too hygroscopic to measure).

IR absorption spectrum (NaCl cell, cm$^{-1}$): 2970, 1495, 1380, 1260, 1010, 815.

NMR spectrum (CDCl$_3$, δ value, ppm): 0.93(t, 6H), 1.19–1.93(m, 2H), 2.14(s, 1H), 1.93–2.94(m, 8H), 4.49(s, 1H), 4.82(d, 1H), 6.10(d, 1H), 6.53–7.46(m, 7H).

Elemental analysis of dihydrochloride:

| | C (%) | H (%) | N (%) |
|---|---|---|---|
| Calcd. for C$_{21}$H$_{29}$Cl$_2$FN$_2$O: | 60.72 | 7.04 | 6.74 |
| Found | 60.68 | 7.03 | 6.85 |

Compound 4

2-methyl-11-{3-(diethylamino)propyl}amino-6,11-dihydrodibenz [b,e] oxepin m.p.: (dihydrochloride being too hygroscopic to measure).

IR absorption spectrum (NaCl cell, cm$^{-1}$): 2970, 1500, 1225, 1125, 1015, 820.

NMR spectrum (CDCl$_3$, δ value, ppm): 0.93(t, 6H), 1.22–1.88(m, 2H), 2.23(s, 3H), 1.88–2.85(m, 9H), 4.48(s, 1H), 4.79(d, 1H), 6.22(d, 1H), 6.52–7.45(m, 7H).

Elemental analysis of dihydrochloride:

| | C (%) | H (%) | N (%) |
|---|---|---|---|
| Calcd. for C$_{22}$H$_{32}$Cl$_2$N$_2$O: | 64.23 | 7.84 | 6.81 |
| Found: | 64.05 | 8.01 | 6.59 |

Compound 5

2-chloro-11-{3-(diethylamino)propyl}amino-6,11-dihydrodibenz [b,e] oxepin m.p.: (dihydrochloride being too hygroscopic to measure)

IR absorption spectrum: (NaCl cell, cm$^{-1}$): 2970, 1480, 1255, 1115, 1005, 820.

NMR spectrum (CDCl$_3$, δ value, ppm): 0.94(t, 6H), 1.25–1.88(m, 2H), 2.04(s, 1H), 1.95–2.95(m, 8H), 4.51(s, 1H), 4.81(d, 1H), 6.34(d, 1H), 6.61–7.55(m, 7H).

Elemental analysis of dihydrochloride:

|  | C (%) | H (%) | N (%) |
| --- | --- | --- | --- |
| Calcd. for C$_{21}$H$_{29}$Cl$_3$N$_2$O: | 58.41 | 6.77 | 6.49 |
| Found: | 58.27 | 6.92 | 6.39 |

Compound 6

4-methyl-11-{3-(diethylamino)propyl}amino-6,11-dihydrodibenz [b,e] oxepin m.p.: (dihydrochloride being too hygroscopic to measure).

IR absorption spectrum (NaCl cell, cm$^{-1}$): 2970, 1475, 1380, 1205, 1090, 1015.

NMR spectrum (CDCl$_3$, δ value, ppm): 0.92(t, 6H), 1.22–1.89(m, 2H), 2.21(s, 3H), 1.89–2.79(m, 9H), 4.50(s, 1H), 4.83(d, 1H), 6.10(d, 1H), 6.52–7.42(m, 7H).

Elemental analysis of dihydrochloride:

|  | C (%) | H (%) | N (%) |
| --- | --- | --- | --- |
| Calcd. for C$_{22}$H$_{32}$Cl$_2$N$_2$O: | 64.23 | 7.84 | 6.81 |
| Found: | 63.98 | 7.67 | 7.02 |

Compound 7

2-methoxy-11-{3-(diethylamino)propyl}amino-6,11-dihydrodibenz [b,e] oxepin m.p.: (dihydrochloride being too hygroscopic to measure).

IR absorption spectrum (NaCl cell, cm$^{-1}$): 2970, 1500, 1380, 1260, 1045, 815.

NMR spectrum (CCl$_4$, δ value, ppm): 0.89(t, 6H), 1.16–1.79(m, 2H), 1.95(s, 1H). 1.79–2.96(m, 8H), 2.63(s, 3H), 4.39(s, 1H), 4.71(d, 1H), 6.03(d, 1H), 6.33–7.36(m, 7H).

Elemental analysis of dihydrochloride:

|  | C (%) | H (%) | N (%) |
| --- | --- | --- | --- |
| Calcd. for C$_{22}$H$_{32}$Cl$_2$N$_2$O$_2$: | 61.82 | 7.55 | 6.55 |
| Found: | 61.97 | 7.38 | 6.60 |

Compound 8

2-methyl-11-{2-(diethylamino)ethyl}amino-6,11-dihydrodibenz [b,e] oxepin m.p.: (dihydrochloride being too hygroscopic to measure).

IR absorption spectrum (NaCl cell, cm$^{-1}$): 2960, 1500, 1260, 1230, 1010, 815.

NMR spectrum (CDCl$_3$, δ value, ppm): 0.94(t, 6H), 2.23(s, 3H), 2.12–2.85(m, 9H), 4.50(s, 1H), 4.79(d, 1H), 6.19(d, 1H), 6.55–7.35 (m, 7H).

Elemental analysis of dihydrochloride:

|  | C (%) | H (%) | N (%) |
| --- | --- | --- | --- |
| Calcd. for C$_{21}$H$_{30}$Cl$_2$N$_2$O: | 63.47 | 7.61 | 7.05 |
| Found: | 63.46 | 7.48 | 7.11 |

Compound 9

2-fluoro-11-{2-(diethylamino)ethyl}amino-6,11-dihydrodibenz [b,e] oxepin m.p.: (dihydrochloride being too hygroscopic to measure).

IR absorption spectrum (NaCl cell, cm$^{-1}$): 2970, 1495, 1380, 1260, 1015, 815.

NMR spectrum (CDCl$_3$, δ value, ppm): 0.94(t, 6H), 1.76–2.82(m, 9H), 4.53(s, 1H), 4.84(d, 1H), 6.10(d, 1H), 6.46–7.39(m, 7H).

Elemental analysis of dihydrochloride:

|  | C (%) | H (%) | N (%) |
| --- | --- | --- | --- |
| Calcd. for C$_{20}$H$_{27}$Cl$_2$FN$_2$O: | 59.85 | 6.78 | 6.98 |
| Found: | 60.01 | 6.95 | 6.81 |

Compound 10

2-chloro-11-{2-(diethylamino)ethyl}amino-6,11-dihydrodibenz [b,e] oxepin m.p.: (dihydrochloride being too hygroscopic to measure).

IR absorption spectrum (NaCl cell, cm$^{-1}$): 2970, 1480, 1260, 1120, 1010, 820.

NMR spectrum (CDCl$_3$, δ value, ppm): 0.93(t, 6H), 1.80–2.80(m, 9H), 4.49(s, 1H), 4.78(d, 1H), 6.30(d, 1H), 6.60–7.43(m, 7H).

Elemental analysis of tartrate:

|  | C (%) | H (%) | N (%) |
| --- | --- | --- | --- |
| Calcd. for C$_{24}$H$_{31}$ClN$_2$O$_7$: | 58.24 | 6.31 | 5.66 |
| Found: | 58.09 | 6.50 | 5.64 |

Compound 11

2-(1-methyl)propyl-11-{2-(diethylamino)-ethyl}amino-6,11-dihydrodibenz [b,e] oxepin m.p.: (dihydrochloride being too hygroscopic to measure).

IR absorption spectrum (NaCl cell, cm$^{-1}$): 2960, 1500, 1230, 1120, 1010, 825.

NMR spectrum (CCl$_4$, δ value, ppm): 0.81(t, 3H), 0.94(t, 6H), 1.18(d, 3H), 1.00–1.85 (m, 2H), 1.98–2.85(m, 10H), 4.41(s, 1H), 4.66 (d, 1H), 6.31(d, 1H), 6.51–7.31(m, 7H).

Elemental analysis of dihydrochloride:

|  | C (%) | H (%) | N (%) |
| --- | --- | --- | --- |
| Calcd. for C$_{24}$H$_{36}$Cl$_2$N$_2$O: | 65.59 | 8.26 | 6.37 |
| Found: | 65.80 | 8.44 | 6.16 |

Compound 12

4-methyl-11-{2-(diethylamino)ethyl}amino-6,11-dihydrodibenz [b,e] oxepin m.p.: (dihydrochloride being too hygroscopic to measure).

IR absorption spectrum (NaCl cell, cm$^{-1}$): 2970, 1470, 1375, 1200, 1085, 1010.

NMR spectrum (CDCl$_3$, δ value, ppm): 0.92(t, 6H), 2.20(s, 3H), 1.63-3.03(m, 9H), 4.52(s, 1H), 4.85(d, 1H), 6.07(d, 1H), 6.50-7.50 (m, 7H).

Elemental analysis of dihydrochloride:

|  | C (%) | H (%) | N (%) |
|---|---|---|---|
| Calcd. for C$_{21}$H$_{30}$Cl$_2$N$_2$O: | 63.47 | 7.61 | 7.05 |
| Found: | 63.58 | 7.70 | 7.02 |

Compound 13

2-methoxy-11-{2-(diethylamino)ethyl}amino-6,11-dihydrodibenz [b,e] oxepin m.p.: (dihydrochloride being too hygroscopic to measure).

IR absorption spectrum (NaCl cell, cm$^{-1}$): 2970, 1500, 1380, 1260, 1045, 815.

NMR spectrum (CDCl$_3$, δ value, ppm): 0.93(t, 6H), 1.74-2.84(m, 9H), 3.69(s, 3H), 4.50(s, 1H), 4.84(d, 1H), 5.96(d, 1H), 6.50-7.40 (m, 7H).

Elemental analysis of dihydrochloride:

|  | C (%) | H (%) | N (%) |
|---|---|---|---|
| Calcd. for C$_{21}$H$_{30}$Cl$_2$N$_2$O$_2$: | 61.02 | 7.32 | 6.78 |
| Found: | 60.99 | 7.27 | 6.90 |

Compound 14

2-methyl-11-{3-(dimethylamino)propyl}amino-6,11-dihydrodibenz [b,e] oxepin m.p.: (dihydrochloride) 187° C. (d.).

IR absorption spectrum (NaCl cell, cm$^{-1}$): 2940, 1500, 1460, 1260, 1015, 820.

NMR spectrum (CDCl$_3$, δ value, ppm): 2.15(s, 6H), 2.25(s, 3H), 1.17-2.80(m, 7H), 4.51(s, 1H), 4.83(d, 1H), 6.19(d, 1H), 6.67-7.37 (m, 7H).

Elemental analysis of dihydrochloride:

|  | C (%) | H (%) | N (%) |
|---|---|---|---|
| Calcd. for C$_{20}$H$_{28}$Cl$_2$N$_2$O: | 62.66 | 7.36 | 7.31 |
| Found: | 62.60 | 7.27 | 7.55 |

Compound 15

2-ethyl-11-{3-dimethylamino)propyl}amino-6,11-dihydrodibenz [b,e] oxepin m.p.: (dihydrochloride being too hygroscopic to measure)

IR absorption spectrum (NaCl cell, cm$^{-1}$): 2930, 1500, 1230, 1125, 1010, 830.

NMR spectrum (CDCl$_3$, δ value, ppm): 1.19(t, 3H), 1.40-1.90(m, 2H), 2.13(s, 6H), 1.97-2.90(m, 7H), 4.50(s, 1H), 4.79(d, 1H), 6.19(d, 1H), 6.67-7.47(m, 7H).

Elemental analysis of dihydrochloride:

|  | C (%) | H (%) | N (%) |
|---|---|---|---|
| Calcd. for C$_{21}$H$_{30}$Cl$_2$N$_2$O: | 63.47 | 7.61 | 7.05 |
| Found: | 63.42 | 7.49 | 7.11 |

Compound 16

2-methyl-11-{2-(dimethylamino)ethyl}amino-6,11-dihydrodibenz [b,e] oxepin m.p.: (dihydrochloride) 144°-147° C.

IR absorption spectrum (NaCl cell, cm$^{-1}$): 2940, 1500, 1265, 1125, 1015, 820.

NMR spectrum (CDCl$_3$, δ value, ppm): 210(s, 6H), 2.22(s, 3H), 1.90-2.87(m, 5H), 4.48(s, 1H), 4.79(d, 1H), 6.19(d, 1H), 6.83-7.44 (m, 7H).

Elemental analysis of dihydrochloride:

|  | C (%) | H (%) | N (%) |
|---|---|---|---|
| Calcd. for C$_{19}$H$_{26}$Cl$_2$N$_2$O: | 61.79 | 7.10 | 7.58 |
| Found: | 61.70 | 7.04 | 7.69 |

Compound 17

2-ethyl-11-{2-(dimethylamino)ethyl}amino-6,11-dihydrodibenz [b,e] oxepin m.p.: (dihydrochloride being too hygroscopic to measure).

IR absorption spectrum (NaCl cell, cm$^{-1}$): 2960, 1500, 1230, 1125, 1015, 825.

NMR spectrum (CCl$_4$, δ value, ppm): 1.18(t, 3H), 2.08(s, 6H), 1.89-2.82(m, 7H), 4.40(s, 1H), 4.65(d, 1H), 6.29(d, 1H), 6.49-7.36(m, 7H).

Elemental analysis of dihydrochloride:

|  | C (%) | H (%) | N (%) |
|---|---|---|---|
| Calcd. for C$_{20}$H$_{28}$Cl$_2$N$_2$O: | 62.66 | 7.36 | 7.31 |
| Found: | 62.51 | 7.28 | 7.34 |

Compound 18

2-fluoro-11-{2-(dimethylamino)ethyl}amino-6,11-dihydrodibenz [b,e] oxepin m.p.: (dihydrochloride) 192° C. (d.).

IR absorption spectrum (NaCl cell, cm$^{-1}$): 2940, 1495, 1260, 1140, 1010, 815.

NMR spectrum (CDCl$_3$, δ value, ppm): 2.09(s, 6H), 1.86-2.86(m, 5H), 4.48(s, 1H) 4.80(d, 1H), 6.07(d, 1H), 6.49-7.39(m, 7H).

Elemental analysis of dihydrochloride:

|  | C (%) | H (%) | N (%) |
|---|---|---|---|
| Calcd. for C$_{18}$H$_{23}$Cl$_2$FN$_2$O: | 57.92 | 6.21 | 7.50 |
| Found: | 58.03 | 6.34 | 7.29 |

Compound 19

2-chloro-11-{2-(dimethylamino)ethyl}amino-6,11-dihydrodibenz [b,e] oxepin m.p.: (tartrate) 85°-88° C.

IR absorption spectrum (NaCl cell, cm$^{-1}$): 2820, 1480, 1255, 1115, 1005, 820.

NMR spectrum (CDCl$_3$, δ value, ppm): 2.05(s, 6H), 1.82–2.82(m, 5H), 4.47(s, 1H), 4.77(d, 1H), 6.30(d, 1H), 6.56–7.42(m, 7H).

Elemental analysis of tartrate:

|  | C (%) | H (%) | N (%) |
|---|---|---|---|
| Calcd. for C$_{22}$H$_{27}$ClN$_2$O$_7$: | 56.59 | 5.83 | 6.00 |
| Found: | 56.68 | 6.01 | 5.88 |

Compound 20

2-methyl-11-(3-quinuclidinyl)amino-6,11-dihydrodibenz [b,e] oxepin m.p.: (dihydrochloride) 165° C. (d.).

IR absorption spectrum (NaCl cell, cm$^{-1}$): 2970, 1500, 1380, 1230, 1050, 820.

NMR spectrum (CDCl$_3$, δ value, ppm): 2.24(s, 3H), 0.84–3.14(m, 13H), 4.52(s, 1H), 4.78 & 4.79(twin d, 1H), 6.13 & 6.25(twin d, 1H) 6.51–7.37(m, 7H).

Elemental analysis of dihydrochloride:

|  | C (%) | H (%) | N (%) |
|---|---|---|---|
| Calcd. for C$_{22}$H$_{28}$Cl$_2$N$_2$O: | 64.86 | 6.93 | 6.88 |
| Found: | 65.01 | 7.03 | 7.00 |

Compound 21

2-ethyl-11-(3-quinuclidinyl)amino-6,11-dihydrodibenz [b,e] oxepin m.p.: (dihydrochloride) 149° C. (d.).

IR absorption spectrum (NaCl cell, cm$^{-1}$): 2930, 1500, 1320, 1230, 1120, 1015.

NMR spectrum (CCl$_4$+CDCl$_3$, δ value, ppm): 1.19(t, 3H), 0.74–3.18(m, 15H), 4.53(s, 1H), 4.78(d, 1H), 6.16 & 6.27(twin d, 1H), 6.48–7.41(m, 7H).

Elemental analysis of dihydrochloride:

|  | C (%) | H (%) | N (%) |
|---|---|---|---|
| Calcd. for C$_{23}$H$_{30}$Cl$_2$N$_2$O: | 65.56 | 7.18 | 6.65 |
| Found: | 65.44 | 7.03 | 6.77 |

Compound 22

2-fluoro-11-(3-quinuclidinyl)amino-6,11-dihydrodibenz [b,e] oxepin m.p.: (dihydrochloride) 188° C. (d.).

IR absorption spectrum (NaCl cell, cm$^{-1}$): 2930, 1500, 1260, 1140, 1015, 820.

NMR spectrum (CCl$_4$+d$_6$-DMSO, δ value, ppm): 0.62–2.09(m, 13H), 4.55(s, 1H), 4.79(d, 1H) 6.04 & 6.14(twin d, 1H), 6.39–7.42(m, 7H).

Elemental analysis of dihydrochloride:

|  | C (%) | H (%) | N (%) |
|---|---|---|---|
| Calcd. for C$_{21}$H$_{25}$Cl$_2$FN$_2$O: | 61.32 | 6.13 | 6.81 |
| Found: | 61.18 | 6.13 | 7.02 |

Compound 23

2-chloro-11-(3-quinuclidinyl)amino-6,11-dihydrodibenzo [b,e] oxepin m.p.: (dihydrochloride) 155° C. (d.).

IR absorption spectrum (KBr tablet, cm$^{-1}$): 2940, 1485, 1260, 1115, 1005, 820.

NMR spectrum (CDCl$_3$, δ value, ppm): 0.78–3.38(m, 13H), 4.54(s, 1H), 4.80(d, 1H), 6.28 & 6.38(twin d, 1H), 6.62–7.55(m, 7H).

Elemental analysis of dihydrochloride:

|  | C (%) | H (%) | N (%) |
|---|---|---|---|
| Calcd. for C$_{21}$H$_{25}$Cl$_3$N$_2$O: | 58.96 | 5.89 | 6.55 |
| Found: | 60.01 | 6.03 | 6.29 |

Compound 24

2-methoxy-11-(3-quinuclidinyl)amino-6,11-dihydrodibenz [b,e] oxepin m.p.: (dihydrochloride) 185° C. (d.).

IR absorption spectrum (KBr tablet, cm$^{-1}$): 2930, 1495, 1260, 1205, 1040, 815.

NMR spectrum (CDCl$_3$, δ value, ppm): 0.81–3.24(m, 13H), 3.68(s, 3H), 4.48(s, 1H), 4.79(d, 1H), 5.85 & 5.98(twin d, 1H), 6.48–7.41 (m, 7H).

Elemental analysis of dihydrochloride:

|  | C (%) | H (%) | N (%) |
|---|---|---|---|
| Calcd. for C$_{22}$H$_{28}$Cl$_2$N$_2$O$_2$: | 62.41 | 6.67 | 6.62 |
| Found: | 62.55 | 6.83 | 6.41 |

Compound 25

2-methyl-11-{2-(1-piperazinyl)ethyl}amino-6,11-dihydrodibenz [b,e] oxepin m.p.: (trihydrochloride) 143° C. (d.).

IR absorption spectrum (NaCl cell, cm$^{-1}$): 2940, 1500, 1225, 1125, 1050, 820.

NMR spectrum (CDCl$_3$, δ value, ppm): 2.23(s, 3H), 1.52–3.05(m, 14H), 4.45(s, 1H), 4.80(d, 1H), 6.08(d, 1H), 6.45–7.38(m, 7H).

Elemental analysis of trihydrochloride:

|  | C (%) | H (%) | N (%) |
|---|---|---|---|
| Calcd. for C$_{21}$H$_{30}$Cl$_3$N$_3$O: | 56.45 | 6.77 | 9.40 |
| Found: | 56.18 | 6.98 | 9.21 |

Compound 26

2-ethyl-11-{2-(1-piperazinyl)ethyl}amino-6,11-dihydrodibenz [b,e] oxepin m.p.: (trihydrochloride) 170° C. (d.).

IR absorption spectrum (NaCl cell, cm$^{-1}$): 2940, 1500, 1260, 1125, 1015, 825.

NMR spectrum (CDCl$_3$, δ value, ppm) 1.18(t, 3H), 2.03–2.99(m, 16H), 4.48(s, 1H), 4.82(d, 1H), 6.10(d, 1H), 6.59–7.46(m, 7H).

Elemental analysis of trihydrochloride:

|  | C (%) | H (%) | N (%) |
|---|---|---|---|
| Calcd. for C$_{22}$H$_{32}$Cl$_3$N$_3$O: | 57.34 | 7.00 | 9.12 |
| Found: | 57.08 | 6.85 | 9.22 |

Compound 27

2-methyl-11-(1-ethyl-3-piperidyl)amino-6,11-dihydrodibenz [b,e] oxepin m.p.: (dihydrochloride) 202° C. (d.).

IR absorption spectrum (NaCl cell, cm$^{-1}$): 2930, 1500, 1265, 1230, 1015, 820.

NMR spectrum (CDCl$_3$, δ value, ppm): 2.21(s, 3H), 0.50–3.04(m, 14H), 4.64(s, 1H), 4.76(d, 1H), 6.24 & 6.29(twin d, 1H), 6.50–7.57(m, 7H).

Elemental analysis of dihydrochloride:

|  | C (%) | H (%) | N (%) |
|---|---|---|---|
| Calcd. for C$_{22}$H$_{30}$Cl$_2$N$_2$O: | 64.54 | 7.39 | 6.84 |
| Found: | 64.77 | 7.48 | 6.71 |

Compound 28

2-methyl-11-{(1-ethyl-2-pyrrolidinyl)methyl}-amino-6,11-dihydrodibenz [b,e] oxepin m.p.: (dihydrochloride) 170° C. (d.).

IR absorption spectrum (dihydrochloride, KBr tablet, cm$^{-1}$): 2650, 1630, 1435, 1215, 1030, 840.

NMR spectrum (CDCl$_3$, δ value, ppm): 1.02(t, 3H), 2.23(s, 3H), 1.30–3.35(m, 12H), 4.49(s, 1H), 4.78(d, 1H), 6.31(d, 1H), 6.62–7.42(m, 7H).

Elemental analysis of dihydrochloride:

|  | C (%) | H (%) | N (%) |
|---|---|---|---|
| Calcd. for C$_{22}$H$_{30}$Cl$_2$N$_2$O: | 64.54 | 7.39 | 6.84 |
| Found: | 64.55 | 7.31 | 7.01 |

Compound 29

2-methyl-11-(4-methyl-1-piperazinyl)amino-6,11-dihydrodibenz [b,e] oxepin m.p.: (trihydrochloride being too hygroscopic to measure).

IR absorption spectrum (NaCl cell, cm$^{-1}$): 2930, 1500, 1260, 1125, 1015, 820.

NMR spectrum (CDCl$_3$, δ value, ppm): 2.21(s, 3H), 2.25(s, 3H), 2.95(s, 1H), 2.06–3.36(m, 8H), 4.71(s, 1H), 4.75(d, 1H), 6.21(d, 1H), 6.53–7.46(m, 7H).

Elemental analysis of trihydrochloride:

|  | C (%) | H (%) | N (%) |
|---|---|---|---|
| Calcd. for C$_{20}$H$_{28}$Cl$_3$N$_3$O: | 55.50 | 6.52 | 9.71 |
| Found: | 55.28 | 6.47 | 10.00 |

Compound 30

2-fluoro-11-{(1,4-benzodioxane-2-)methyl}-amino-6,11-dihydrodibenz [b,e] oxepin m.p.: (hydrochloride) 199°–202° C.

IR absorption spectrum (hydrochloride, KBr tablet, cm$^{-1}$): 1595, 1495, 1265, 1205, 1020, 750.

NMR spectrum (hydrochloride, d$_6$-DMSO, δ value, ppm): 3.00–4.50(m, 7H), 4.98(d, 1H), 5.63(s, 1H), 5.77(d, 1H), 6.80–7.70(m, 11H).

Elemental analysis of hydrochloride:

|  | C (%) | H (%) | N (%) |
|---|---|---|---|
| Calcd. for C$_{23}$H$_{21}$ClFNO$_3$: | 66.75 | 5.12 | 3.38 |
| Found: | 66.89 | 5.17 | 3.52 |

Compound 31

2-fluoro-11-{bis-(4-fluorophenyl)methyl}amino-6,11-dihydrodibenz [b,e] oxepin m.p.: (hydrochloride) 105°–108° C.

IR absorption spectrum (NaCl cell, cm$^{-1}$): 3030, 1610, 1500, 1230, 830, 735.

NMR spectrum (CCl$_4$, δ value, ppm): 2.61(s, 1H), 4.29(s, 1H), 4.55(s, 1H), 4.83(d, 1H), 5.81(d, 1H), 6.50–7.50(m, 15H).

Elemental analysis of hydrochloride:

|  | C (%) | H (%) | N (%) |
|---|---|---|---|
| Calcd. for C$_{27}$H$_{21}$ClF$_3$NO: | 69.30 | 4.52 | 2.99 |
| Found: | 69.17 | 4.38 | 3.01 |

Compound 32

2-fluoro-11-{(1-methyl-3-phenyl)propyl}amino-6,11-dihydrodibenz [b,e] oxepin m.p.: (hydrochloride 183°–186° C.

IR absorption spectrum (hydrochloride, KBr tablet, cm$^{-1}$): 1490, 1430, 1200, 1015, 830, 750.

NMR spectrum (CCl$_4$, δ value, ppm): 1.08 & 0.98(twin d, 3H), 1.30–2.80(m, 6H), 4.55(s, 1H), 4.71(d, 1H), 6.18 & 6.35(twin d, 1H), 6.60–7.30(m, 12H).

Elemental analysis of hydrochloride:

|  | C (%) | H (%) | N (%) |
|---|---|---|---|
| Calcd. for C$_{24}$H$_{25}$ClFNO: | 72.44 | 6.33 | 3.52 |
| Found: | 72.40 | 6.27 | 3.52 |

Compound 33

2-fluoro-11-{2-(diphenylmethyloxy)ethyl}amino-6,11-dihydrodibenz [b,e] oxepin m.p.: (hydrochloride) 184°–187° C.

IR absorption spectrum (hydrochloride, KBr tablet, cm$^{-1}$): 3020, 1495, 1205, 1095, 1020, 755.

NMR spectrum (CCl$_4$+d$_6$-DMSO, δ value, ppm): 2.29(s, 1H), 2.74(t, 2H), 3.52(t, 2H), 4.69(s, 1H), 4.75(d, 1H), 5.29(s, 1H), 6.10(d, 1H), 6.70–7.50(m, 17H).

Elemental analysis of hydrochloride:

|  | C (%) | H (%) | N (%) |
|---|---|---|---|
| Calcd. for C$_{29}$H$_{27}$ClFNO$_2$: | 73.18 | 5.72 | 2.94 |
| Found: | 73.22 | 5.80 | 2.87 |

Compound 34

2-fluoro-11-{2-(dibenzylamino)ethyl}amino-6,11-dihydrodibenz [b,e] oxepin m.p.: (dihydrochloride) 196°–198° C.

IR absorption spectrum (dihydrochloride, KBr tablet, cm$^{-1}$): 2930, 1495, 1430, 1205, 1020, 755.

NMR spectrum (CCl$_4$, δ value, ppm): 200(s, 1H), 2.45(s, 4H), 3.42(s, 4H), 4.21(s, 1H), 4.61(d, 1H), 6.09(d, 1H), 6.60–7.40(m, 17H).

Elemental analysis of dihydrochloride:

|  | C (%) | H (%) | N (%) |
|---|---|---|---|
| Calcd. for C$_{30}$H$_{31}$Cl$_2$FN$_2$O: | 68.57 | 5.95 | 5.33 |
| Found: | 68.74 | 6.02 | 5.09 |

Compound 35

2-ethyl-11-(2-piperidinoethyl)amino-6,11-dihydrodibenz [b,e] oxepin m.p.: 98°–101° C.

IR absorption spectrum (KBr tablet, cm$^{-1}$): 2930, 1500, 1260, 1125, 1015, 825.

NMR spectrum (CDCl$_3$, δ value, ppm): 1.18(t, 3H), 1.17–1.83(m, 6H), 2.10–2.90(m, 11H), 4.50(s, 1H), 4.79(d, 1H), 6.15(d, 1H), 6.63–7.43(m, 7H).

Elemental analysis:

|  | C (%) | H (%) | N (%) |
|---|---|---|---|
| Calcd. for C$_{23}$H$_{30}$N$_2$O: | 78.81 | 8.63 | 7.99 |
| Found: | 78.74 | 8.55 | 8.03 |

Compound 36

2-methyl-11-[2-(2-pyridyl)ethyl]amino-6,11-dihydrodibenz [b,e] oxepin m.p.: (dihydrochloride) 184° C. (d.).

IR absorption spectrum (NaCl cell, cm$^{-1}$): 2930, 1595, 1500, 1230, 1010, 820.

NMR spectrum (CDCl$_3$, δ value, ppm): 2.13(s, 1H), 2.21(s, 3H), 2.90(s, 4H), 4.53(s, 1H), 4.70(d, 1H), 6.16(d, 1H), 6.60–7.70(m, 10H), 8.30–8.60(m, 1H).

Elemental analysis of dihydrochloride:

|  | C (%) | H (%) | N (%) |
|---|---|---|---|
| Calcd. for C$_{22}$H$_{24}$Cl$_2$N$_2$O: | 65.51 | 6.00 | 6.94 |
| Found: | 65.38 | 5.98 | 7.02 |

EXAMPLE 37

Preparation of compound 37

2-methyl-11-[4-(2-hydroxyethyl)-1-piperazinyl]-6,11-dihydrodibenz [b,e] oxepin

In this example, 3.7 g of crude crystals of 2-methyl-11-chloro-6,11-dihydrodibenz [b,e] oxepin obtained from 3.6 g of 2-methyl-6,11-dihydrodibenz [b,e] oxepinone-11 in the same manner as in Example 1 are dissolved in 60 ml of toluene and the solution is dropwise added to a solution of 9.8 g of 1-(2-hydroxyethyl) piperazine in 20 ml of toluene, followed by heating for 2 hours at 80° C. After completion of the reaction, 30 ml of water is added thereto, and the pH of the solution is adjusted to 2.0 with concentrated hydrochloric acid. Then, a toluene layer is discarded, and 20 ml of ethyl ether is added to an aqueous layer, followed by readjusting the pH of the solution to 10.5 with a 10 N sodium hydroxide aqueous solution. The aqueous layer is discarded, and the ethyl ether layer is dehydrated and concentrated under reduced pressure. The residue is purified through silica gel chromatography. Concentration of the main fractions gives 4.0 g of 2-methyl-11-[4-(2-hydroxyethyl)-1-piperazinyl]-6,11-dihydrodibenz [b,e] oxepin [compound 37] in an oily free base in a yield of 79%.

m.p.: (fumarate) 172°–175° C.

IR absorption spectrum (NaCl cell, cm$^{-1}$): 2950, 1500, 1235, 1120, 1010, 760.

NMR spectrum (CDCl$_3$, δ value, ppm): 2.21(s, 3H), 2.56(s, 8H), 2.06–2.73(m, 2H), 3.58(t, 2H), 3.83(s, 1H), 3.86(s, 1H), 4.65(d, 1H), 6.53–7.50(m, 8H).

Elemental analysis of fumarate:

|  | C (%) | H (%) | N (%) |
|---|---|---|---|
| Calcd. for C$_{25}$H$_{30}$N$_2$O$_6$: | 66.06 | 6.65 | 6.16 |
| Found: | 65.88 | 6.39 | 6.08 |

EXAMPLES 38 TO 47

Compounds 38 to 47 are obtained in a similar manner to that in Example 37 except that Compound II shown in Table 3 and amine are used instead of 2-methyl-6,11-dihydrodibenz [b,e] oxepinone-11 (Compound II) and 1-(2-hydroxyethyl)piperazine in Example 37.

TABLE 3

| Example | Compound II name | used amount (g) | Amine name | used amount (g) | Obtained amount of the desired compound (g) |
|---|---|---|---|---|---|
| 38 | 2-ethyl-6,11-dihydrodibenz [b,e]oxepinone-11 | 2.4 | N—(2-hydroxyethyl)piperazine | 2.6 | 2.8 |
| 39 | 2-fluoro-6,11-dihydrodibenz [b,e]oxepinone-11 | 2.3 | N—(2-hydroxyethyl)piperazine | 2.6 | 2.9 |
| 40 | 2-chloro-6,11-dihydrodibenz [b,e]oxepinone-11 | 2.4 | N—(2-hydroxyethyl)piperazine | 2.6 | 2.6 |
| 41 | 4-methyl-6,11-dihydrodibenz [b,e]oxepinone-11 | 2.2 | N—(2-hydroxyethyl)piperazine | 2.6 | 2.5 |
| 42 | 4-phenyl-6,11-dihydrodibenz [b,e]oxepinone-11 | 2.9 | N—(2-hydroxyethyl)piperazine | 2.6 | 2.0 |
| 43 | 2-fluoro-6,11-dihydrodibenz [b,e]oxepinone-11 | 4.6 | N—{bis-(4-fluorophenyl)}-methylpiperazine | 6.0 | 3.4 |
| 44 | 2-methyl-6,11-dihydrodibenz [b,e]oxepinone-11 | 4.4 | N—(2-aminoethyl) piperazine | 5.2 | 1.7 |
| 45 | 2-ethyl-6,11-dihydrodibenz [b,e]oxepinone-11 | 4.8 | N—(2-aminoethyl) piperazine | 5.2 | 2.7 |
| 46 | 2-fluoro-6,11-dihydrodibenz [b,e]oxepinone-11 | 4.6 | N—(2-aminoethyl) piperazine | 2.6 | 4.0 |

TABLE 3-continued

| | Compound II | | Amine | | Obtained amount of |
|---|---|---|---|---|---|
| Example | name | used amount (g) | name | used amount (g) | the desired compound (g) |
| 47 | 4-phenyl-6,11-dihydrodibenz [b,e]oxepinone-11 | 2.9 | 1-methylpiperazine | 2.0 | 3.1 |

Compound 38

2-ethyl-11[4-(2-hydroxyethyl)-1-piperazinyl]-6,11-dihydrodibenz [b,e] oxepin m.p.: (fumarate) 179° C. (d.).

IR absorption spectrum (NaCl cell, cm$^{-1}$): 2955, 1500, 1225, 1140, 1005, 755.

NMR spectrum (fumarate, d$_6$-DMSO, δ value, ppm): 1.11(t, 3H), 2.14–2.84(m, 12H), 3.52(t, 2H), 3.98(s, 1H), 4.70(d, 1H), 6.27–7.50(m, 10H), 8.62(broad s, 3H).

Elemental analysis of fumarate:

| | C (%) | H (%) | N (%) |
|---|---|---|---|
| Calcd. for C$_{26}$H$_{32}$N$_2$O$_6$: | 66.65 | 6.88 | 5.98 |
| Found: | 66.39 | 6.87 | 6.21 |

Compound 39

2-fluoro-11-{4-(2-hydroxyethyl)-1-piperazinyl)}-6,11-dihydrodibenz [b,e] oxepin m.p.: (dihydrochloride) 140° C. (d.).

IR absorption spectrum (NaCl cell, cm$^{-1}$): 2810, 1495, 1255, 1140, 1000, 760.

NMR spectrum (CDCl$_3$, δvalue, ppm): 2.40(s, 8H), 2.07–2.63(m, 2H), 2.83(s, 1H), 3.57(t, 2H), 3.82(s, 1H), 4.64(d, 1H), 6.43–7.43(m, 8H).

Elemental analysis of dihydrochloride:

| | C (%) | H (%) | N (%) |
|---|---|---|---|
| Calcd. for C$_{20}$H$_{25}$Cl$_2$FN$_2$O$_2$: | 57.84 | 6.07 | 6.74 |
| Found: | 57.80 | 5.96 | 7.00 |

Compound 40

2-chloro-11-{4-(2-hydroxyethyl)-1-piperazinyl}-6,11-dihydrodibenz [b,e] oxepin m.p.: 90°–93° C.

IR absorption spectrum (KBr tablet, cm$^{-1}$): 2810, 1485, 1255, 1140, 1000, 815.

NMR spectrum (CDCl$_3$, δ value, ppm): 2.42(s, 8H), 2.71(s, 1H), 2.16–2.93(m, 2H), 3.58(t, 2H), 3.80(s, 1H), 4.66(d, 1H), 6.56–7.39(m, 8H).

Elemental analysis:

| | C (%) | H (%) | N (%) |
|---|---|---|---|
| Calcd. for C$_{20}$H$_{23}$ClN$_2$O$_2$: | 66.94 | 6.46 | 7.81 |
| Found: | 67.05 | 6.22 | 8.00 |

Compound 41

4-methyl-11-{4-(2-hydroxyethyl)-1-piperazinyl}-6,11-dihydrodibenz [b,e] oxepin m.p.: (dihydrochloride) 161°–164° C.

IR absorption spectrum (NaCl cell, cm$^{-1}$): 2940, 1465, 1310, 1140, 1085, 1005.

NMR spectrum (CDCl$_3$, δ value, ppm): 2.14(s, 3H), 2.40(s, 8H), 1.94–2.74(m, 3H), 3.55(t, 2H), 3.87(s, 1H), 4.75(d, 1H), 6.44–7.41(m, 8H).

Elememtal analysis of dihydrochloride:

| | C (%) | H (%) | N (%) |
|---|---|---|---|
| Calcd. for C$_{21}$H$_{28}$Cl$_2$N$_2$O$_2$: | 61.32 | 6.86 | 6.81 |
| Found: | 61.30 | 7.00 | 6.71 |

Compound 42

4-phenyl-11-{4-(2-hydroxyethyl)-1-piperazinyl}-6,11-dihydrodibenz [b,e] oxepin m.p.: (dihydrochloride being too hygroscopic to measure).

IR absorption spectrum (dihydrochloride, KBr tablet, cm$^{-1}$): 3020, 1635, 1435, 1210, 1020, 765.

NMR spectrum (CDCl$_3$, δ value, ppm): 2.40(s, 8H), 1.94–2.74(m, 3H), 3.56(t, 2H), 3.92(s, 1H), 4.64(d, 1H), 6.43–7.62(m, 13H).

Elemental analysis of dihydrochloride:

| | C (%) | H (%) | N (%) |
|---|---|---|---|
| Calcd. for C$_{26}$H$_{30}$Cl$_2$N$_2$O$_2$: | 65.96 | 6.39 | 5.92 |
| Found: | 66.01 | 6.52 | 6.01 |

Compound 43

2-fluoro-11-[4-{bis-(4-fluorophenyl)}methyl-1-piperazinyl]-6,11-dihydrodibenz [b,e] oxepin m.p.: 185°–188° C.

IR absorption spectrum (KBr tablet, cm$^{-1}$): 2810, 1605, 1495, 1220, 1005, 820.

NMR spectrum (d$_6$-acetone, δ value, ppm): 2.35(s, 8H), 3.98(s, 1H), 4.30(s, 1H), 4.68(d, 1H), 6.70–7.70(m, 16H).

Elemental analysis:

| | C (%) | H (%) | N (%) |
|---|---|---|---|
| Calcd. for C$_{31}$H$_{27}$F$_3$N$_2$O: | 74.38 | 5.44 | 5.60 |
| Found: | 74.39 | 5.29 | 5.61 |

Compound 44

2-methyl-11-{4-(2-aminoethyl)-1-piperazinyl}-6,11-dihydrodibenz [b,e] oxepin m.p.: (trihydrochloride) 146° C. (d.).

IR absorption spectrum (KBr tablet, cm$^{-1}$) 2810, 1495, 1225, 1125, 1005, 815.

NMR spectrum (CDCl$_2$, δ value, ppm): 2.20(s, 3H), 2.34(s, 8H), 1.65–2.92(m, 6H), 3.80(s, 1H), 4.63(d, 1H), 6.42–7.45(m, 8H).

Elemental analysis of trihydrochloride:

| | C (%) | H (%) | N (%) |
|---|---|---|---|
| Calcd. for $C_{21}H_{30}Cl_3N_3O$: | 56.45 | 6.77 | 9.40 |
| Found: | 56.23 | 7.01 | 9.15 |

Compound 45

2-ethyl-11-{4-(2-aminoethyl)-1-piperazinyl)}-6,11-dihydrodibenz [b,e] oxepin m.p.: (trihydrochloride) 130°–133° C.

IR absorption spectrum (NaCl cell, cm$^{-1}$): 2960, 1495, 1225, 1125, 1005, 825.

NMR spectrum (CDCl$_3$, δ value, ppm): 1.18(t, 3H), 2.30(s, 2H), 2.37(s, 8H). 1.74–2.77(m, 6H), 3.85(s, 1H), 4.64(d, 1H), 6.51–7.51(m, 8H).

Elemental analysis of trihydrochloride:

| | C (%) | H (%) | N (%) |
|---|---|---|---|
| Calcd. for $C_{22}H_{32}Cl_3N_3O$: | 57.34 | 7.00 | 9.12 |
| Found: | 57.38 | 6.89 | 8.98 |

Compound 46

2-fluoro-11-{4-(2-aminoethyl)-1-piperazinyl}-6,11-dihydrodibenz [b,e] oxepin m.p.: (trihydrochloride) 134°–137° C.

IR absorption spectrum (trihydrochloride, KBr tablet, cm$^{-1}$): 1620, 1500, 1440, 1210, 1020, 760.

NMR spectrum (CDCl$_3$, δ value, ppm): 1.70–3.20(m, 14H), 3.77(s, 1H), 4.62(d, 1H), 6.40–7.50(m, 8H).

Elemental analysis of trihydrochloride:

| | C (%) | H (%) | N (%) |
|---|---|---|---|
| Calcd. for $C_{20}H_{27}Cl_3FN_3O$: | 53.29 | 6.04 | 9.32 |
| Found: | 53.01 | 6.08 | 9.09 |

Compound 47

4-phenyl-11-(4-methyl-1-piperazinyl)-6,11-dihydrodibenz [b,e] oxepin m.p.: (dihydrochloride) 132°–135° C.

IR absorption spectrum (NaCl cell, cm$^{-1}$): 2800, 1430, 1225, 1000, 850, 760.

NMR spectrum (CDCl$_3$, δ value, ppm): 2.21(s, 3H), 2.39(s, 8H), 3.97(s, 1H), 4.64(d, 1H), 6.47–7.57(m, 13H).

Elemental analysis of dihydrochloride:

| | C (%) | H (%) | N (%) |
|---|---|---|---|
| Calcd. for $C_{25}H_{28}Cl_2N_2O$: | 67.72 | 6.36 | 6.32 |
| Found: | 67.55 | 6.09 | 6.30 |

Compound 48

2-cyclohexyl-11-{2-(diethylamino)ethyl}amino-6,11-dihydrodibenz [b,e] oxepin m.p.: (dihydrochloride) 128°–130° C.

IR Absorption spectrum (NaCl cell, cm$^{-1}$): 2930, 1500, 1455, 1260, 1230, 1020.

NMR spectrum (CDCl$_3$, δ value, ppm): 0.93(t, 6H), 0.63–2.07(m, 10H), 2.07–2.80(m, 10H), 4.50(s, 1H), 4.77(d, 1H), 6.13(d, 1H), 6.63–7.36(m, 7H).

Elemental analysis of dihydrochloride:

| | C (%) | H (%) | N (%) |
|---|---|---|---|
| Calcd. for $C_{26}H_{38}Cl_2N_2O$: | 67.08 | 8.23 | 6.02 |
| Found: | 67.06 | 8.26 | 5.99 |

Compound 49

2-fluoro-11-{3-(dimethylamino)propyl}amino-6,11-dihydrodibenz [b,e] oxepin m.p.: (dihydrochloride) 199° C. (d.).

IR absorption spectrum (NaCl cell, cm$^{-1}$): 2940, 1495, 1260, 1225, 1195, 760.

NMR spectrum (CDCl$_3$, δ value, ppm): 1.32–1.90(m, 2H), 2.13(s, 6H), 1.93–2.83(m, 5H), 4.50(s, 1H), 4.85(d, 1H), 6.06(d, 1H), 6.56–7.49(m, 7H).

Elemental analysis of dihydrochloride:

| | C (%) | H (%) | N (%) |
|---|---|---|---|
| Calcd. for $C_{19}H_{25}Cl_2FN_2O$: | 58.92 | 6.51 | 7.23 |
| Found: | 58.74 | 6.52 | 7.24 |

Compound 50

2-chloro-11-{3-(dimethylamino)propyl}amino-6,11-dihydrodibenz [b,e] oxepin m.p.: (dihydrochloride) 200° C. (d.).

IR absorption spectrum (NaCl cell, cm$^{-1}$) 2940, 2830, 1485, 1255, 1230, 1010.

NMR spectrum (CDCl$_3$, δ value, ppm): 1.36–1.86(m, 2H), 2.13(s, 6H), 1.86–2.83(m, 5H), 4.50(s, 1H), 4.80(d, 1H), 6.29(d, 1H), 6.60–7.34(m, 7H).

Elemental analysis of dihydrochloride:

| | C (%) | H (%) | N (%) |
|---|---|---|---|
| Calcd. for $C_{19}H_{25}Cl_3N_2O$: | 56.51 | 6.24 | 6.94 |
| Found: | 56.54 | 6.25 | 6.83 |

Compound 51

2-(1-methyl)propyl-11-(3-quinuclidinyl)amino-6,11-dihydrodibenz [b,e] oxepin m.p.: (dihydrochloride) 140°–142° C.

IR absorption spectrum (NaCl cell, cm$^{-1}$) 2950, 1500, 1455, 1260, 1230, 755.

NMR spectrum (CDCl$_3$, δ value, ppm): 0.81(t, 3H), 1.20(d, 3H), 0.50–3.30(m, 16H), 4.56(s, 1H), 4.78 & 4.81(twin d, 1H), 6.17 & 6.30(twin d, 1H), 6.60–7.46(m, 7H).

Elemental analysis of dihydrochloride:

| | C (%) | H (%) | N (%) |
|---|---|---|---|
| Calcd. for $C_{25}H_{34}Cl_2N_2O$: | 66.81 | 7.62 | 6.23 |
| Found: | 66.85 | 7.64 | 6.21 |

Compound 52

2-(1,1-dimethyl)ethyl-11-(3-quinuclidinyl)amino-6,11-dihydrodibenz [b,e] oxepin m.p.: (dihydrochloride) 145°–149° C.

IR absorption spectrum (NaCl cell, cm$^{-1}$) 2950, 1500, 1255, 1230, 1130, 1015.

NMR spectrum (CDCl$_3$, δ value, ppm): 1.29(s, 9H), 0.71–3.21(m, 13H), 4.58(s, 1H), 4.77 & 4.80(twin d, 1H), 6.19 & 6.32(twin d, 1H), 6.64–7.47(m, 7H).

Elemental analysis of dihydrochloride:

|  | C (%) | H (%) | N (%) |
|---|---|---|---|
| Calcd. for C$_{25}$H$_{34}$Cl$_2$N$_2$O: | 66.80 | 7.63 | 6.23 |
| Found: | 66.78 | 7.65 | 6.24 |

Compound 53

2-(1,1-dimethyl)propyl-11-(3-quinuclidinyl)amino-6,11-dihydrodibenz [b,e] oxepin m.p.: (dihydrochloride) 141°–144° C.

IR absorption spectrum (NaCl cell, cm$^{-1}$) 2930, 2860, 1500, 1260, 1230, 730.

NMR spectrum (CDCl$_3$, δ value, ppm): 0.68(t, 3H), 1.25(s, 6H), 0.92–3.11(m, 15H), 4.58(s, 1H), 4.75 & 4.82 (twin d, 1H), 6.19 & 6.31 (twin d, 1H), 6.59–7.46(m, 7H).

Elemental analysis of dihydrochloride:

|  | C (%) | H (%) | N (%) |
|---|---|---|---|
| Calcd. for C$_{26}$H$_{36}$Cl$_2$N$_2$O: | 67.37 | 7.83 | 6.04 |
| Found: | 67.39 | 7.84 | 6.03 |

Compound 54

2-cyclohexyl-11-(3-quinuclidinyl)amino-6,11-dihydrodibenz [b,e] oxepin m.p.: (dihydrochloride) 140°–143° C.

IR absorption spectrum (KBr tablet, cm$^{-1}$): 2920, 2850, 1500, 1455, 1230, 760.

NMR spectrum (CDCl$_3$, δ value, ppm): 0.82–3.18(m, 24H), 4.55(s, 1H), 4.81(d, 1H), 6.16 & 6.30(twin d, 1H), 6.62–7.35(m, 7H).

Elemental analysis of dihydrochloride:

|  | C (%) | H (%) | N (%) |
|---|---|---|---|
| Calcd. for C$_{27}$H$_{36}$Cl$_2$N$_2$O: | 68.20 | 7.63 | 5.89 |
| Found: | 68.36 | 7.56 | 5.93 |

Compound 55

2-phenyl-11-(3-quinuclidinyl)amino-6,11-dihydrodibenz [b,e] oxepin m.p.: (dihydrochloride) 148°–150° C.

IR absorption spectrum (NaCl cell, cm$^{-1}$): 2940, 2870, 1485, 1250, 1230, 760.

NMR spectrum (CDCl$_3$, δ value, ppm): 0.86–3.23(m, 13H), 4.69(s, 1H), 4.86(d, 1H), 6.41 & 6.51(twin d, 1H), 6.83–7.81(m, 12H).

Elemental analysis of dihydrochloride:

|  | C (%) | H (%) | N (%) |
|---|---|---|---|
| Calcd. for C$_{27}$H$_{30}$Cl$_2$N$_2$O: | 69.08 | 6.44 | 5.97 |
| Found: | 69.07 | 6.41 | 6.01 |

Compound 56

4-methyl-11-(3-quinuclidinyl)amino-6,11-dihydrodibenz [b,e] oxepin m.p.: (dihydrochloride) 150°–153° C.

NMR spectrum (CDCl$_3$, δ value, ppm): 2.22(s, 3H), 0.82–3.16(m, 13H), 4.55(s, 1H), 4.87(d, 1H), 5.98 & 6.13(twin d, 1H, 6.45–7.32(m, 7H).

Elemental analysis of dihydrochloride:

|  | C (%) | H (%) | N (%) |
|---|---|---|---|
| Calcd. for C$_{22}$H$_{28}$Cl$_2$N$_2$O: | 64.86 | 6.93 | 6.88 |
| Found: | 64.92 | 6.96 | 6.76 |

Compound 57

4-phenyl-11-(3-quinuclidinyl)amino-6,11-dihydrodibenz [b,e] oxepin m.p.: (dihydrochloride) 153°–155° C.

IR absorption spectrum (KBr tablet, cm$^{-1}$): 2930, 1470, 1435, 1220, 1010, 760.

NMR spectrum (CDCl$_3$, δ value, ppm) 0.90–3.47(m, 13H), 4.61(s, 1H), 4.74(d, 1H), 5.67 & 5.82(twin d, 1H), 6.70–7.93(m, 12H).

Elemental analysis of dihydrochloride:

|  | C (%) | H (%) | N (%) |
|---|---|---|---|
| Calcd. for C$_{27}$H$_{30}$Cl$_2$N$_2$O: | 69.08 | 6.44 | 5.97 |
| Found: | 69.21 | 6.45 | 5.83 |

Compound 58

2-methyl-11-{2-(1-pyrrolidinyl)ethyl}amino-6,11-dihydrodibenz [b,e] oxepin m.p.: (dihydrochloride) 154°–157° C.

IR absorption spectrum (NaCl cell, cm$^{-1}$): 2960, 2790, 1500, 1260, 1230, 1120.

NMR spectrum (CDCl$_3$, δ value, ppm): 1.33–1.93(m, 4H), 2.20(s, 3H), 2.00–2.90(m, 9H), 4.47(s, 1H), 4.75(d, 1H), 6.20(d, 1H), 6.63–7.39(m, 7H).

Elemental analysis of dihydrochloride:

|  | C (%) | H (%) | N (%) |
|---|---|---|---|
| Calcd. for C$_{21}$H$_{28}$Cl$_2$N$_2$O: | 63.79 | 7.14 | 7.09 |
| Found: | 63.84 | 7.12 | 7.10 |

Compound 59

2-methyl-11-(2-morpholinoethyl)amino-6,11-dihydrodibenz [b,e] oxepin m.p.: 100°–102° C.

IR absorption spectrum (KBr tablet, cm$^{-1}$): 2810, 1500, 1260, 1230, 1115, 760.

NMR spectrum (CDCl$_3$, δ value, ppm): 2.24(s, 3H), 2.06–2.83(m, 9H), 3.60(t, 4H), 4.46(s, 1H), 4.81(d, 1H), 6.07(d, 1H), 6.62–7.36(m, 7H).

Elemental analysis:

|  | C (%) | H (%) | N (%) |
|---|---|---|---|
| Calcd. for $C_{21}H_{26}N_2O_2$: | 74.52 | 7.74 | 8.28 |
| Found: | 74.50 | 7.73 | 8.29 |

Compound 60

2-fluoro-11-{2-(3,4-dimethoxyphenyl)ethyl}amino-6,11-dihydrodibenz [b,e] oxepin

M.p.: (dihydrochloride) 222° C. (d.).

IR absorption spectrum NaCl cell, cm$^{-1}$: 2940, 1500, 1260, 1240, 1145, 1030.

NMR spectrum (CDCl$_3$, δ value, ppm): 1.95(s, 1H), 2.52–2.96(m. 4H), 3.75(s, 3H), 3.77)s, 3H), 4.49(s, 1H), 4.78(d, 1H), 5.95(d, 1H), 6.42–7.39(m, 10H).

Elemental analysis of dihydrochloride:

|  | C (%) | H (%) | N (%) |
|---|---|---|---|
| Calcd. for $C_{24}H_{25}ClFNO_3$: | 67.05 | 5.86 | 3.26 |
| Found: | 67.04 | 5.90 | 3.27 |

Compound 61

2-ethyl-11-(5-quinolyl)amino-6,11-dihydrodibenz [b,e] oxepin m.p.: 112°–115° C.

IR absorption spectrum (KBr tablet, cm$^{-1}$): 2960, 1615, 1580, 1480, 1415, 790.

NMR spectrum CDCl$_3$, δ value, ppm): 1.13(t, 3H), 2.13–2.90(m, 2H), 5.01(d, 1H), 5.54(s, 1H), 5.83(d, 1H), 4.63–6.08(broad, 1H), 6.46–7.80(m, 11H), 7.89–8.32(m, 1H), 8.50–8.93(m, 1H).

Elemental analysis:

|  | C (%) | H (%) | N (%) |
|---|---|---|---|
| Calcd. for $C_{25}H_{22}N_2O$: | 81.94 | 6.05 | 7.65 |
| Found: | 81.98 | 6.04 | 7.68 |

Compound 62

2-methyl-11-(5-indolyl)amino-6,11-dihydrodibenz [b,e] oxepin m.p.: (dihydrochloride) 184° C. (d.).

IR absorption spectrum (NaCl cell, cm$^{-1}$): 1500, 1465, 1250, 1225, 820, 755.

NMR spectrum (CDCl$_3$ δ value, ppm): 2.16(s, 3H), 4.17(broad, 1H), 4.95(d, 1H), 5.30(s, 1H), 5.82(d, 1H), 6.10–7.57(m, 12H), 7.77(broad, 1H).

Elemental analysis of dihydrochloride:

|  | C (%) | H (%) | N (%) |
|---|---|---|---|
| Calcd. for $C_{23}H_{22}Cl_2N_2O$: | 66.83 | 5.37 | 6.78 |
| Found: | 66.84 | 5.39 | 6.70 |

Compound 63

2-ethyl-11-{4-(2,2,6,6-tetramethyl)piperidinyl}amino-6,11-dihydrodibenz [b,e] oxepin m.p.: (dihydrochloride) 198° C. (d.).

IR absorption spectrum (NaCl cell, cm$^{-1}$): 2960, 1500, 1260, 1230, 1015, 755.

NMR spectrum (CDCl$_3$, δ value, ppm): 1.03(s, 12H), 1.17(t, 3H), 0.36–2.16(m, 5H), 2.22–3.12(m, 4H), 4.74(s, 1H), 4.77(d, 1H), 6.16(d, 1H), 6.66–7.45(m, 7H).

Elemental analysis of dihydrochloride:

|  | C (%) | H (%) | N (%) |
|---|---|---|---|
| Calcd. for $C_{25}H_{36}Cl_2N_2O$: | 66.50 | 8.04 | 6.21 |
| Found: | 66.64 | 8.11 | 6.07 |

Compound 64

2-methyl-11-[N-{2-(dimethylamino)ethyl}-N-ethyl-]amino-6,11-dihydrodibenz [b,e] oxepin m.p.: (dihydrochloride being too hygroscopic to measure).

IR absorption spectrum (NaCl cell, cm$^{-1}$): 2970, 1500, 1260, 1225, 1015, 755.

NMR spectrum (CDCl$_3$, δ value, ppm): 0.90(t, 3H), 1.99(s, 6H), 2.16(s, 3H), 1.80–2.86 (m, 6H), 4.23(s, 1H), 4.61(d, 1H), 6.49–7.29 (m, 8H).

Elemental analysis of dihydrochloride:

|  | C (%) | H (%) | N (%) |
|---|---|---|---|
| Calcd. for $C_{21}H_{30}Cl_2N_2O$: | 63.47 | 7.61 | 7.05 |
| Found: | 63.42 | 7.62 | 7.07 |

Compound 65

2-methyl-11-(1',3'-dioxoran-2'-spiropiperidino)-6,11-dihydrodibenz [b,e] oxepin m.p.: 115°–118° C.

IR absorption spectrum (KBr tablet, cm$^{-1}$): 2950, 1500, 1260, 1225, 1145, 1070.

NMR spectrum (CDCl$_3$, δ value, ppm): 1.63(t, 4H), 2.20(s, 3H), 2.48(t, 4H), 3.86(s, 5H), 4.65(d, 1H), 6.54–7.37(m, 8H).

Elemental analysis:

|  | C (%) | H (%) | N (%) |
|---|---|---|---|
| Calcd. for $C_{22}H_{25}NO_3$: | 75.18 | 7.17 | 3.99 |
| Found: | 75.21 | 7.13 | 4.02 |

Compound 66

2-ethyl-11-(4-methyl-1-piperazinyl)-6,11-dihydrodibenz [b,e] oxepin m.p.: 97°–99° C.

IR absorption spectrum (KBr tablet, cm$^{-1}$): 2800, 1500, 1290, 1225, 1155, 1005.

NMR spectrum (CDCl$_3$, δ value, ppm): 1.16(t, 3H), 1.85–2.85(m, 13H), 3.82(s, 1H), 4.64(d, 1H), 6.52–7.62(m, 8H).

Elemental analysis:

|  | C (%) | H (%) | N (%) |
|---|---|---|---|
| Calcd. for $C_{21}H_{26}N_2O$: | 78.22 | 8.13 | 8.69 |
| Found: | 78.01 | 7.96 | 8.71 |

Compound 67

2-methyl-11-(4-methyl-1-piperazinyl)-6,11-dihydrodibenz [b,e] oxepin m.p.: (fumarate) 168°–170° C.

IR absorption spectrum (KBr tablet, cm$^{-1}$): 2790, 1500, 1230, 1155, 1010, 760.

NMR spectrum (fumarate, $d_6$-DMSO, $\delta$ value, ppm): 1.88–3.02(m, 14H), 3.98(s, 1H), 4.72(d, 1H), 6.25–8.08(m, 12H).

Elemental analysis of fumarate:

|  | C (%) | H (%) | N (%) |
|---|---|---|---|
| Calcd. for $C_{24}H_{28}N_2O_5$: | 67.91 | 6.65 | 6.60 |
| Found: | 68.02 | 6.66 | 6.41 |

Compound 68

2-methoxy-11-(4-methyl-1-piperazinyl)-6,11-dihydrodibenz [b,e] oxepin m.p.: (fumarate) 167°–170° C.

IR absorption spectrum (NaCl cell, cm$^{-1}$): 2930, 2790, 1495, 1225, 1220, 1145.

NMR spectrum (CDCl$_3$, $\delta$ value, ppm): 2.13(s, 3H), 2.72(s, 8H), 3.70(s, 3H), 4.05(s, 1H), 4.67(d, 1H), 6.20–7.40(m, 8H).

Elemental analysis of fumarate:

|  | C (%) | H (%) | N (%) |
|---|---|---|---|
| Calcd. for $C_{24}H_{28}N_2O_6$: | 65.44 | 6.41 | 6.36 |
| Found: | 65.42 | 6.13 | 6.14 |

Compound 69

2-fluoro-11-(4-methyl-1-piperazinyl)-6,11-dihydrodibenz [b,e] oxepin m.p.: 140°–143° C.

IR absorption spectrum (KBr tablet, cm$^{-1}$): 2790, 1495, 1260, 1140, 1005, 820.

NMR spectrum (CDCl$_3$, $\delta$ value, ppm): 2.22(s, 3H), 2.37(s, 8H), 3.81(s, 1H), 4.67(d, 1H), 6.57–7.51(m, 8H).

Elemental analysis:

|  | C (%) | H (%) | N (%) |
|---|---|---|---|
| Calcd. for $C_{19}H_{21}FN_2O$: | 73.05 | 6.78 | 8.97 |
| Found: | 72.88 | 7.01 | 9.02 |

Compound 70

2-chloro-11-(4-methyl-1-piperazinyl)-6,11-dihydrodibenz [b,e] oxepin m.p.: (dihydrochloride) 258° C. (d).

IR absorption spectrum (dihydrochloride, KBr tablet, cm$^{-1}$): 2600, 1630, 1485, 1255, 1000, 830.

NMR spectrum (CDCl$_3$, $\delta$ value, ppm): 2.21(s, 3H), 2.35(s, 8H), 3.80(s, 1H), 4.66(d, 1H), 6.51–7.67(m, 8H).

Elemental analysis of dihydrochloride:

|  | C (%) | H (%) | N (%) |
|---|---|---|---|
| Calcd. for $C_{19}H_{23}Cl_3N_2O$: | 56.80 | 5.77 | 6.97 |
| Found: | 56.51 | 6.01 | 7.02 |

EXAMPLE 71

Preparation of tablet

A tablet comprising the following components is prepared in a conventional manner.

| Component |  |
|---|---|
| Compound 66 | 30 mg |
| Lactose | 60 mg |
| Potato starch | 30 mg |
| Polyvinyl alcohol | 2 mg |
| Magnesium stearate | 1 mg |
| Tar pigment | q.s. |

EXAMPLE 72

Preparation of powder

A powder comprising the following components is prepared in a conventional manner.

| Component |  |
|---|---|
| Fumarate of compound 67 | 30 mg |
| Lactose | 270 mg |

EXAMPLE 73

Preparation of syrup

A syrup comprising the following components is prepared in a conventional manner.

| Component |  |
|---|---|
| Dihydrochloride of Compound 70 | 300 mg |
| Sucrose | 40 g |
| Methyl para-hydroxybenzoate | 40 mg |
| Propyl para-hydroxybenzoate | 10 mg |
| Strawberry flavour | 0.1 cc |

Water is added to the above components dissolving the above components, until the total volume is 100 cc.

What is claimed is:

1. A dibenz [b,e] oxepin compound represented by the formula:

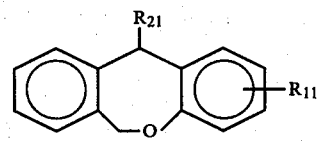

wherein R$_{11}$ represents an alkyl group having 1 to 5 carbon atoms, an alkoxy group having 1 to 5 carbon atoms, a halogen atom, a cyclohexyl group or a phenyl group; and R$_{21}$ represents —HN—(CH$_2$)$_n$—Y, wherein Y represents a quinuclidinyl group and n is 0 or an integer of 1 to 3; and the pharmaceutically acceptable acid addition salts thereof.

2. A dibenz [b,e] oxepin compound according to claim 1 wherein R$_{11}$ represents an alkyl group having 1 to 5 carbon atoms.

3. A dibenz [b,e] oxepin compound according to claim 2 wherein the alkyl group is a methyl group, an ethyl group, a propyl group or a butyl group.

4. A dibenz [b,e] oxepin compound according to claim 3 wherein the alkyl group is a methyl group or an ethyl group.

5. A dibenz [b,e] oxepin compound according to claim 1 wherein $R_{11}$ represents a cyclohexyl group.

6. A dibenz [b,e] oxepin compound according to claim 1 wherein $R_{11}$ represents a phenyl group.

7. 2-methyl-11-(3-quinuclidinyl)amino-6,11-dihydrodibenz [b,e] oxepin.

8. 2-ethyl-11-(3-quinuclidinyl)amino-6,11-dihydrodibenz [b,e] oxepin.

9. 2-phenyl-11-(3-quinuclidinyl)amino-6,11-dihydrodibenz [b,e] oxepin.

* * * * *